US010231798B2

(12) United States Patent
Schuele et al.

(10) Patent No.: US 10,231,798 B2
(45) Date of Patent: Mar. 19, 2019

(54) SKULL CLAMP OPENING APPARATUS AND METHOD

(71) Applicant: pro med instruments GmbH, Freiburg im Breisgau (DE)

(72) Inventors: Matthias E. Schuele, Freiburg (DE); Bernhard Gantner, March (DE)

(73) Assignee: pro med instruments GmbH, Freiburg im Breisgau (DE)

( * ) Notice: Subject to any disclaimer, the term of this patent is extended or adjusted under 35 U.S.C. 154(b) by 564 days.

(21) Appl. No.: 14/075,548

(22) Filed: Nov. 8, 2013

(65) Prior Publication Data

US 2014/0135765 A1 May 15, 2014

Related U.S. Application Data

(60) Provisional application No. 61/844,382, filed on Jul. 9, 2013, provisional application No. 61/724,845, filed on Nov. 9, 2012.

(51) Int. Cl.
*A61B 19/00* (2006.01)
*A61B 90/14* (2016.01)

(52) U.S. Cl.
CPC .................................... *A61B 90/14* (2016.02)

(58) Field of Classification Search
CPC ... A61B 19/203; A61B 90/14; A61B 17/6433; A61G 13/121; A61G 13/101; A61G 15/125; A61G 7/072; A61G 9/1009; B25B 5/04; B25B 5/08; B25B 5/003; B25B 5/10; B25B 5/106; B25B 5/103; B25B 5/20; B25B 5/107; B25B 5/102; B25B 5/02; B25B 5/166; B25B 5/006; B25B 5/06; B25B 1/20; B25B 1/24; B25B 1/08;

(Continued)

(56) References Cited

U.S. PATENT DOCUMENTS 3,099,441 A * 7/1963 Ries ........................ A61B 90/14
5/637
3,654,923 A * 4/1972 Crutchfield .......... A61H 1/0218
602/37

(Continued)

FOREIGN PATENT DOCUMENTS

| JP | S59-183362 U | 12/1984 |
|----|--------------|---------|
| JP | 2002-524131 A | 8/2002 |
| WO | WO 2013/127457 | 9/2013 |

OTHER PUBLICATIONS

International Search Report and Written Opinion dated Jun. 27, 2014 for Application No. PCT/IB2013/003016.

(Continued)

*Primary Examiner* — Eduardo C Robert
*Assistant Examiner* — Tessa Matthews
(74) *Attorney, Agent, or Firm* — Frost Brown Todd LLC

(57) ABSTRACT

A head fixation device in the form of a skull clamp comprises an opening device having an actuator positioned along an upright portion of the skull clamp near where a pin assembly contacts a patient's head for stabilization. The opening device can be actuated such that the relative distance between arms of the skull clamp can be opened, closed, or adjusted. The opening device is substantially positioned within one of the arms of the skull clamp. In some versions the skull clamp further comprises an attachment feature having an offset configuration.

20 Claims, 28 Drawing Sheets

(58) Field of Classification Search
CPC .. B25B 1/103; B25B 1/12; B25B 1/02; B25B 1/04; B25B 1/2463; B25B 1/2468; B25B 1/2473; B25B 1/2478; B25B 1/2484; B25B 1/2405; B25B 27/08; B25B 27/146; B25B 27/26; B25B 13/18; B25B 13/24; B25B 13/26; B25B 13/32; B25B 13/50; B25B 9/00; B25B 9/02; B25B 7/00; B25B 7/14; B23Q 3/06; B23Q 3/00; B23Q 3/02; B23Q 3/205; B23Q 3/103; B23D 51/025; B23D 51/04; B23B 1/22; B23B 1/125; B23B 1/20; B23B 1/24; A43D 67/00; A43D 71/02; A43D 79/00

USPC ................................. 606/57, 130, 53, 54, 59

See application file for complete search history.

(56) References Cited

U.S. PATENT DOCUMENTS

| | | | |
|---|---|---|---|
| 3,835,861 A | 9/1974 | Kees, Jr. et al. | |
| 4,054,279 A * | 10/1977 | Wain | B25B 1/04 269/154 |
| 4,809,534 A * | 3/1989 | Osborn | B25B 1/14 29/751 |
| 5,312,410 A * | 5/1994 | Miller et al. | 606/86 R |
| 5,537,704 A * | 7/1996 | Dinkler | 5/622 |
| 5,758,870 A * | 6/1998 | Weaver | B25B 5/101 269/249 |
| 6,162,222 A * | 12/2000 | Poka et al. | 606/54 |
| 6,179,846 B1 * | 1/2001 | McFadden | A61B 90/14 606/130 |
| D456,510 S | 4/2002 | Spetzler et al. | |
| 6,381,783 B2 | 5/2002 | Reinhardt et al. | |
| 7,661,162 B2 | 2/2010 | Soerensen et al. | |
| 9,844,482 B2 | 12/2017 | Radina et al. | |
| 2006/0190010 A1 * | 8/2006 | Easton | 606/130 |
| 2007/0052145 A1 * | 3/2007 | Cantin | B25B 5/06 269/6 |
| 2007/0250071 A1 * | 10/2007 | Soerensen | A61B 90/14 606/130 |
| 2008/0224375 A1 * | 9/2008 | Mills | B25B 5/04 269/134 |
| 2010/0059064 A1 | 3/2010 | Schüle et al. | |
| 2010/0249780 A1 | 9/2010 | Rolfes | |
| 2011/0092771 A1 | 4/2011 | Hynes | |
| 2011/0221110 A1 * | 9/2011 | Ranieri | B25B 5/04 269/6 |
| 2012/0326375 A1 * | 12/2012 | Chuang | B25B 5/101 269/128 |
| 2013/0081636 A1 * | 4/2013 | Schuele | A61B 90/57 128/845 |
| 2013/0190604 A1 * | 7/2013 | Moffatt | A61B 5/0555 600/411 |

OTHER PUBLICATIONS

Chinese Office Action, The First Office Action, and Search Report dated Mar. 7, 2017 for Application No. CN 201380058442.5, 10 pgs.
Chinese Office Action, The Second Office Action, and Search Report dated Nov. 15, 2017 for Application No. CN 201380058442.5, 15 pgs.
Chinese Office Action, The Third Office Action, dated Jul. 13, 2018 for Application No. CN 201380058442.5, 7 pgs.
European Intention to Grant dated Apr. 4, 2016 for Application No. EP 13836211.6, 60 pgs.
European Search Report and Written Opinion dated Jan. 24, 2017 for Application No. EP 16002084.8, 7 pgs.
European Examination Report dated Oct. 5, 2017 for Application No. EP 16002084.8, 3 pgs.
European Intention to Grant dated Aug. 31, 2018 for Application No. EP 16002084.8, 61 pgs.
Japanese Office Action, Notice of Rejection, dated Aug. 8, 2017 for Application No. JP 2015-541254, 10 pgs.
Japanese Office Action, Notification of Reasons for Refusal, and Search Report by Registered Searching Organization dated Oct. 30, 2018 for Application No. JP 2018-000744, 35 pgs.

* cited by examiner

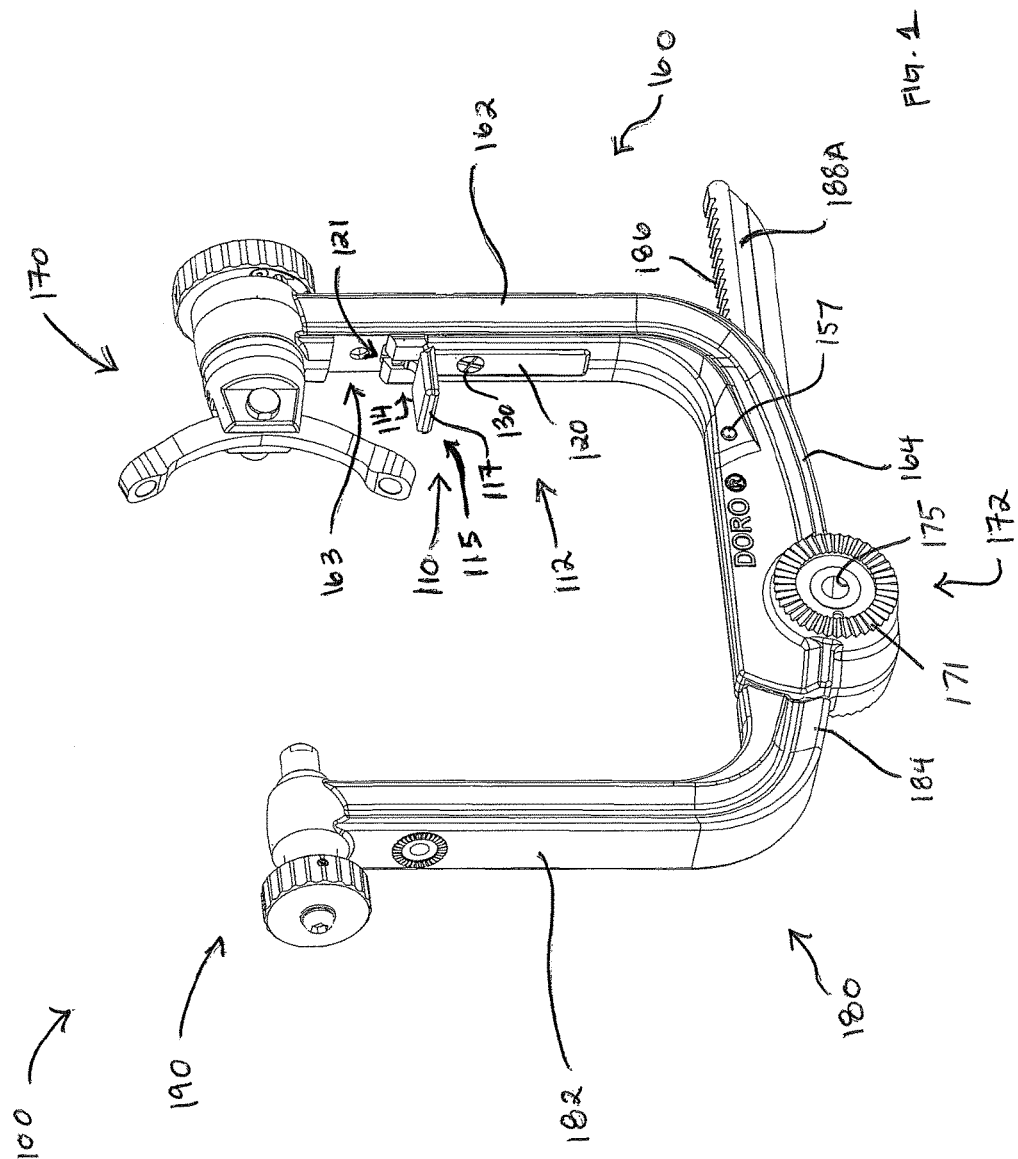

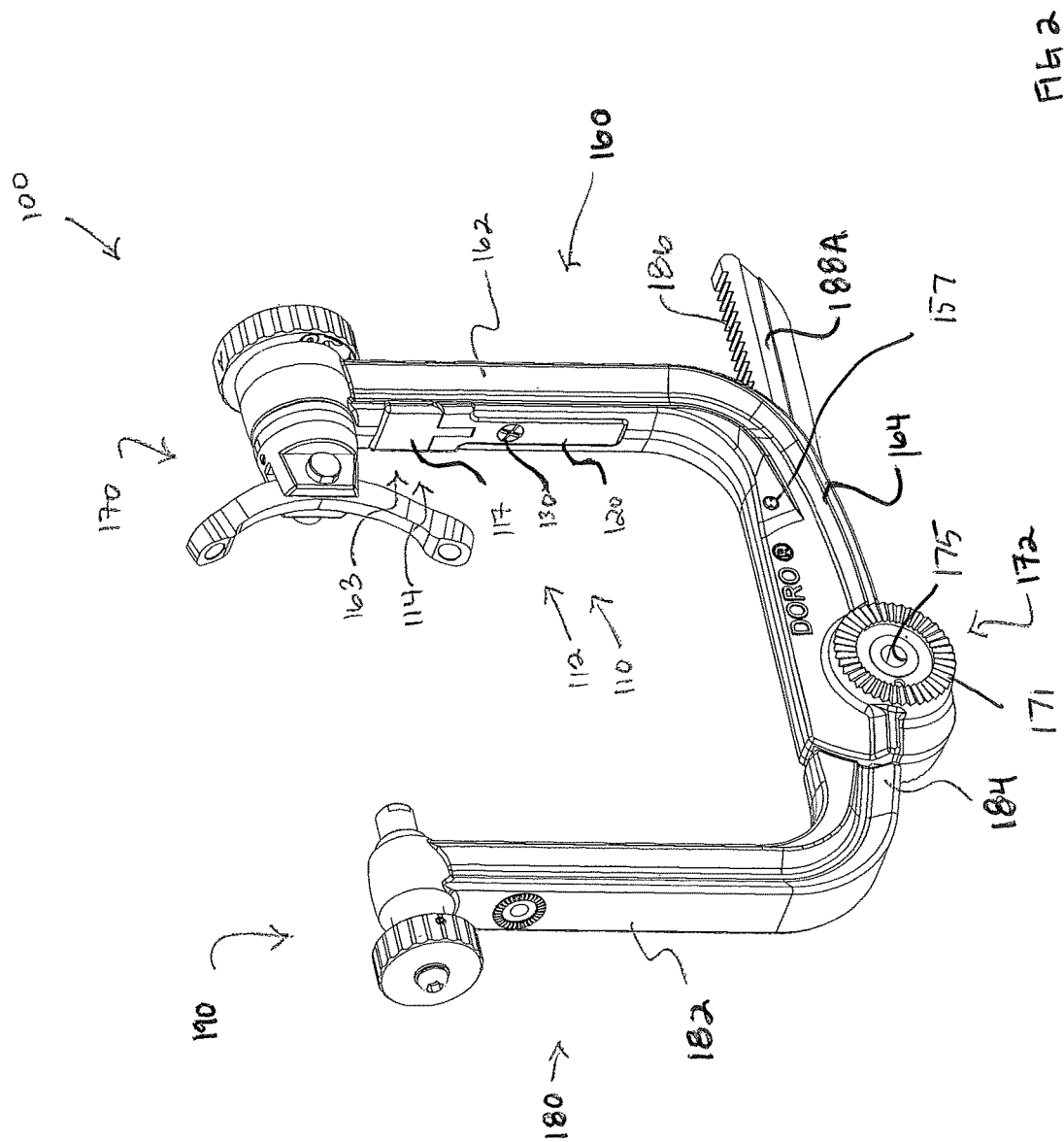

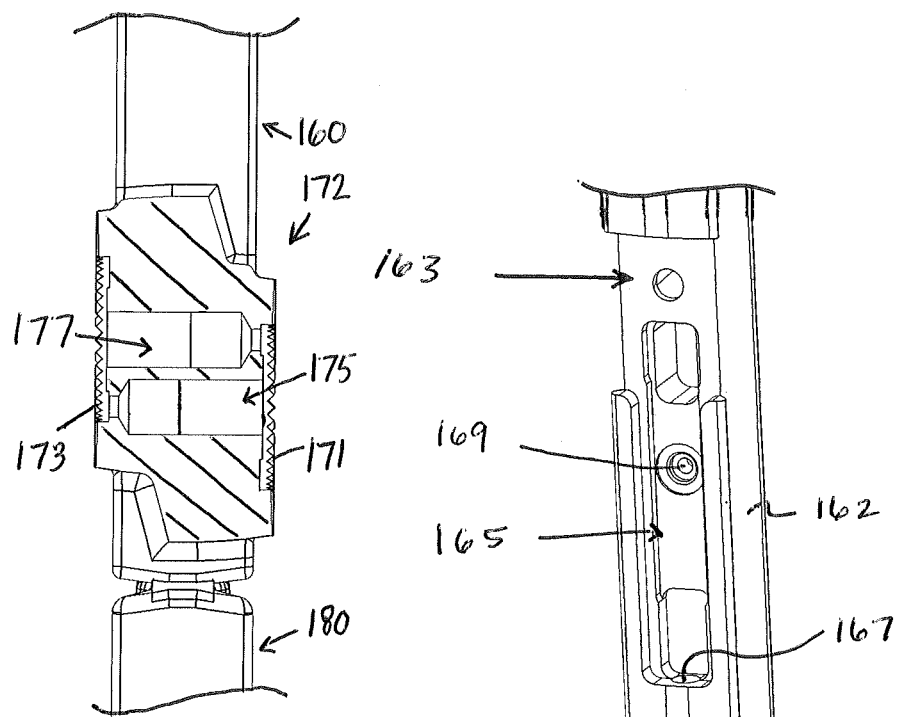
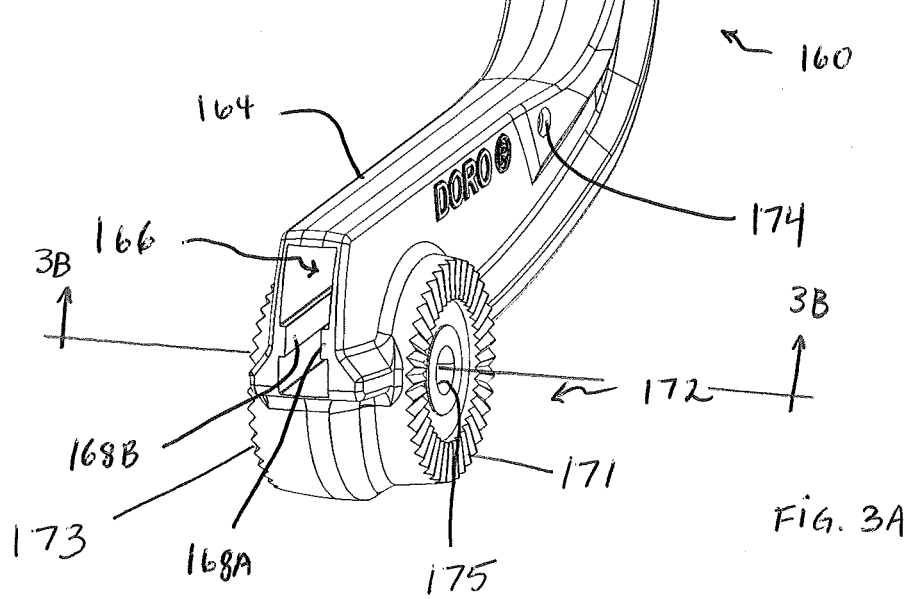

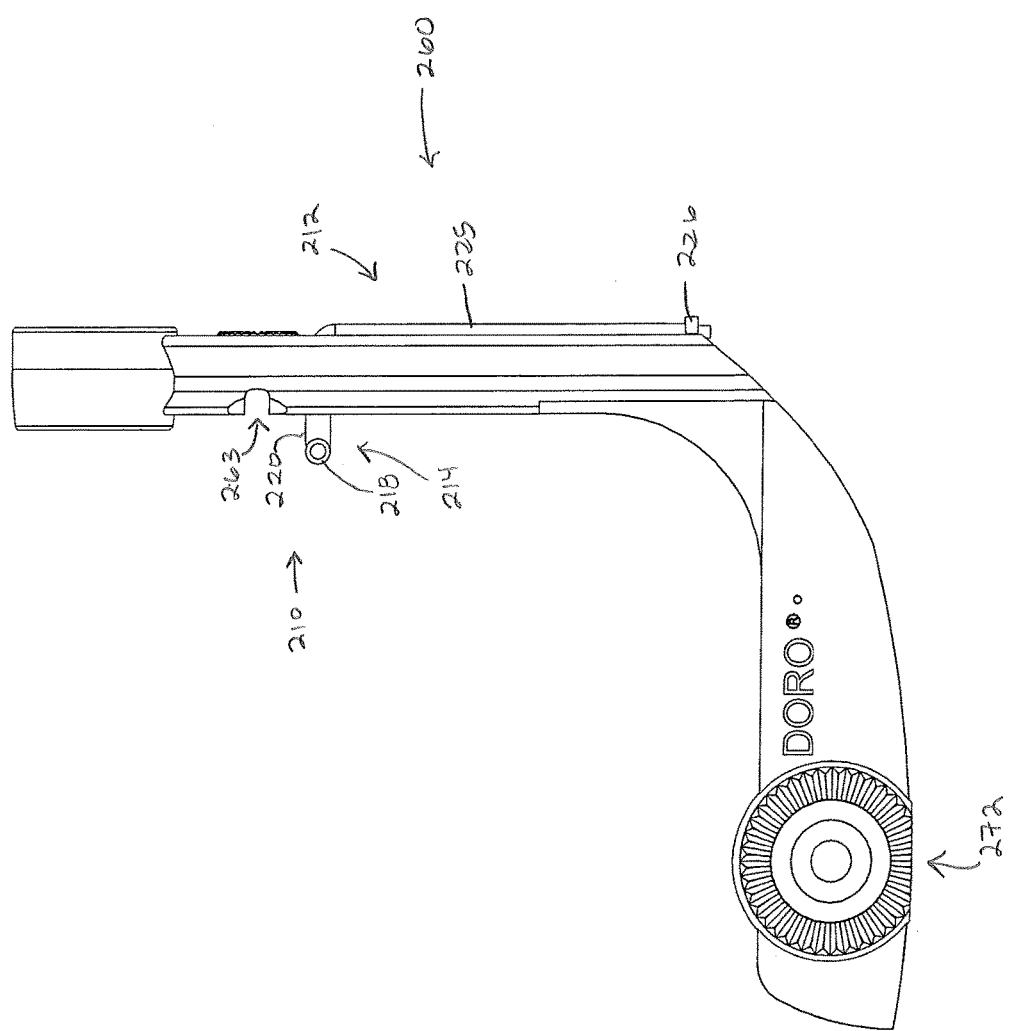

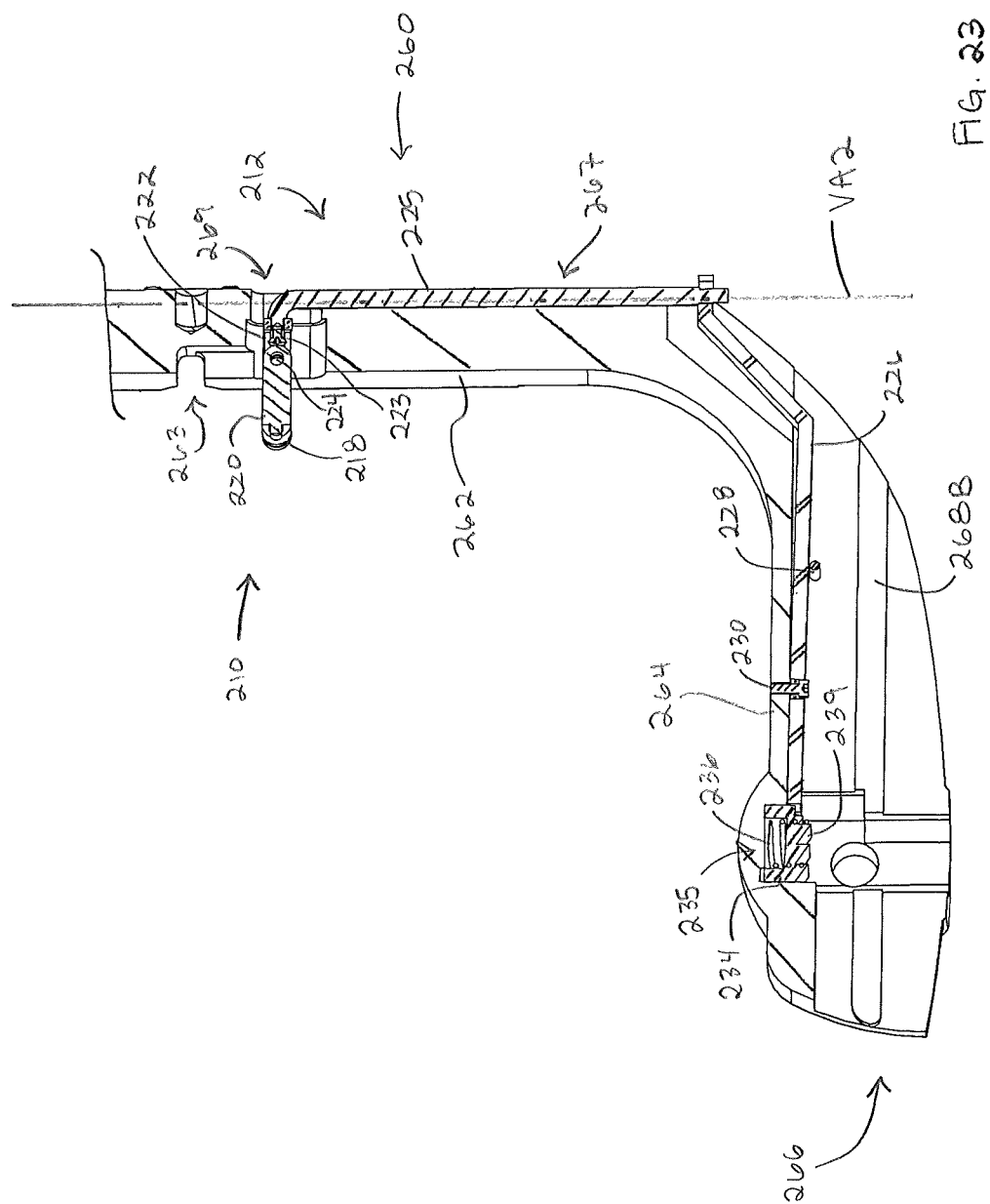

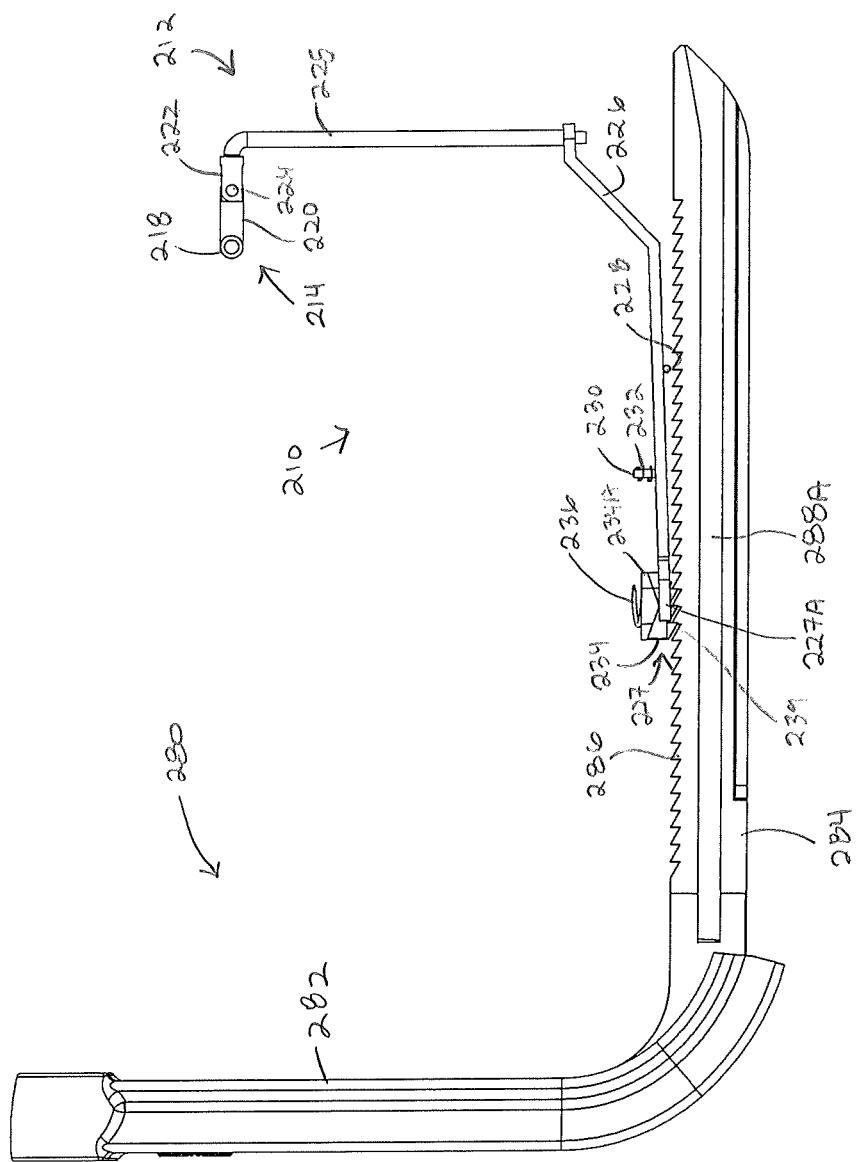

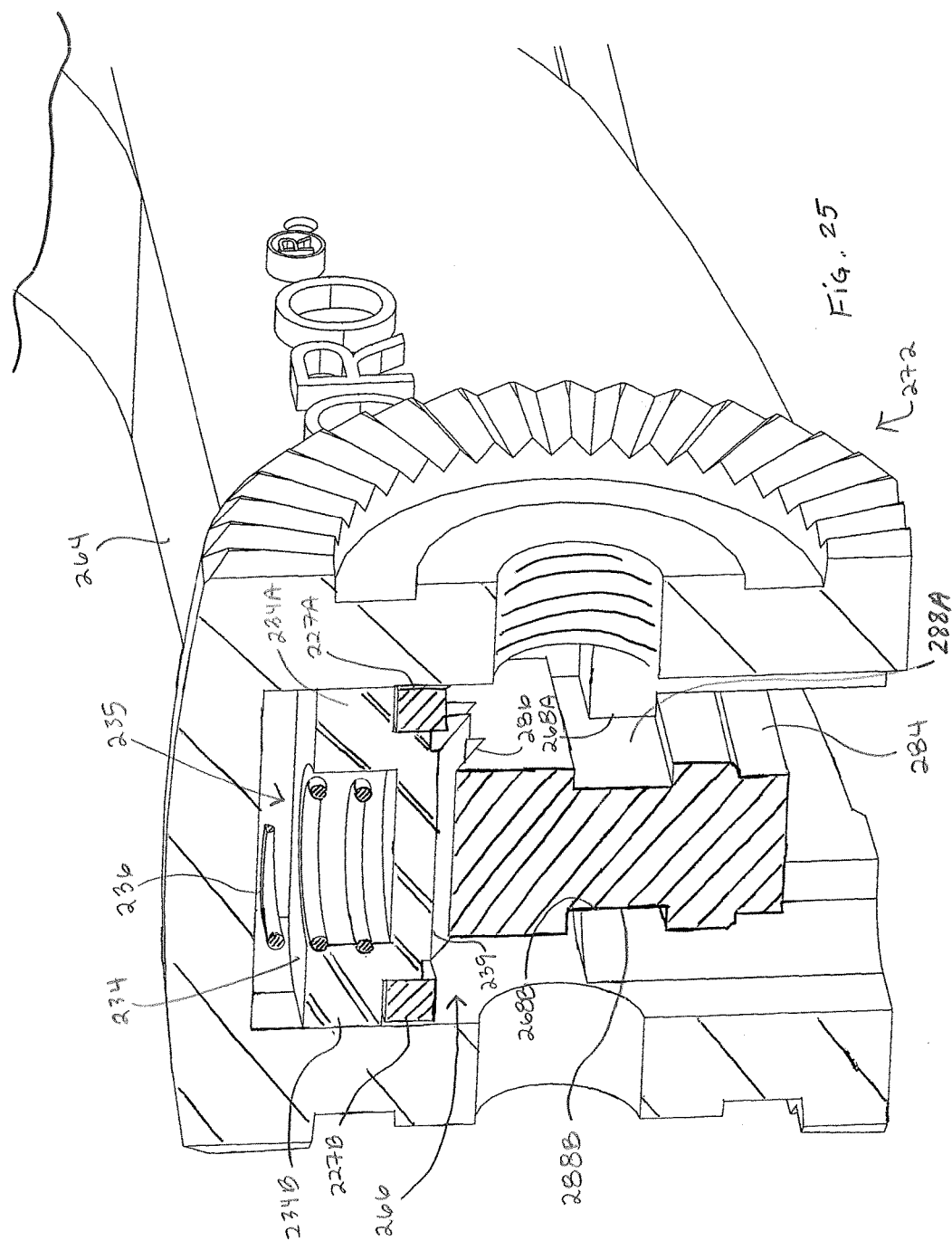

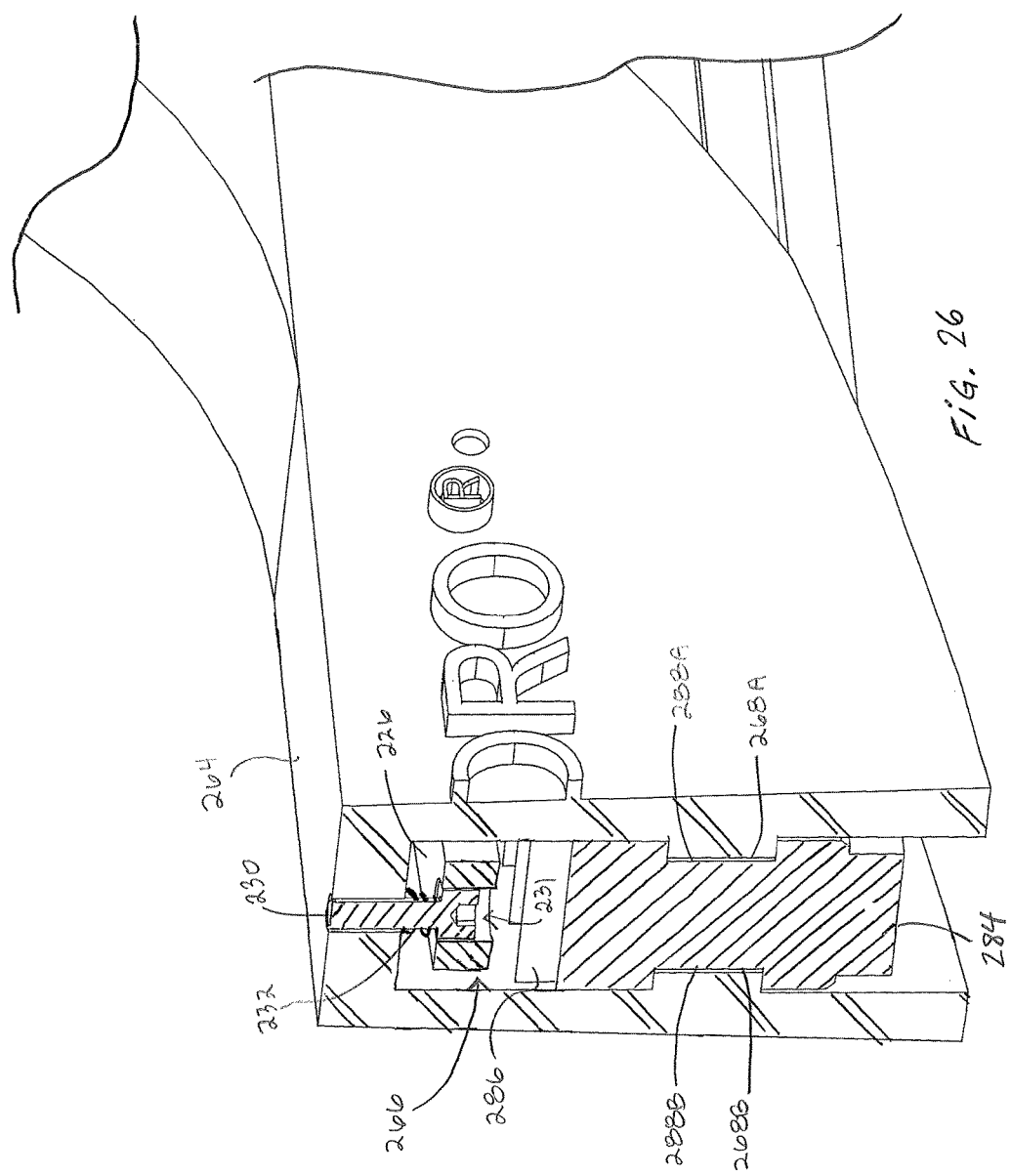

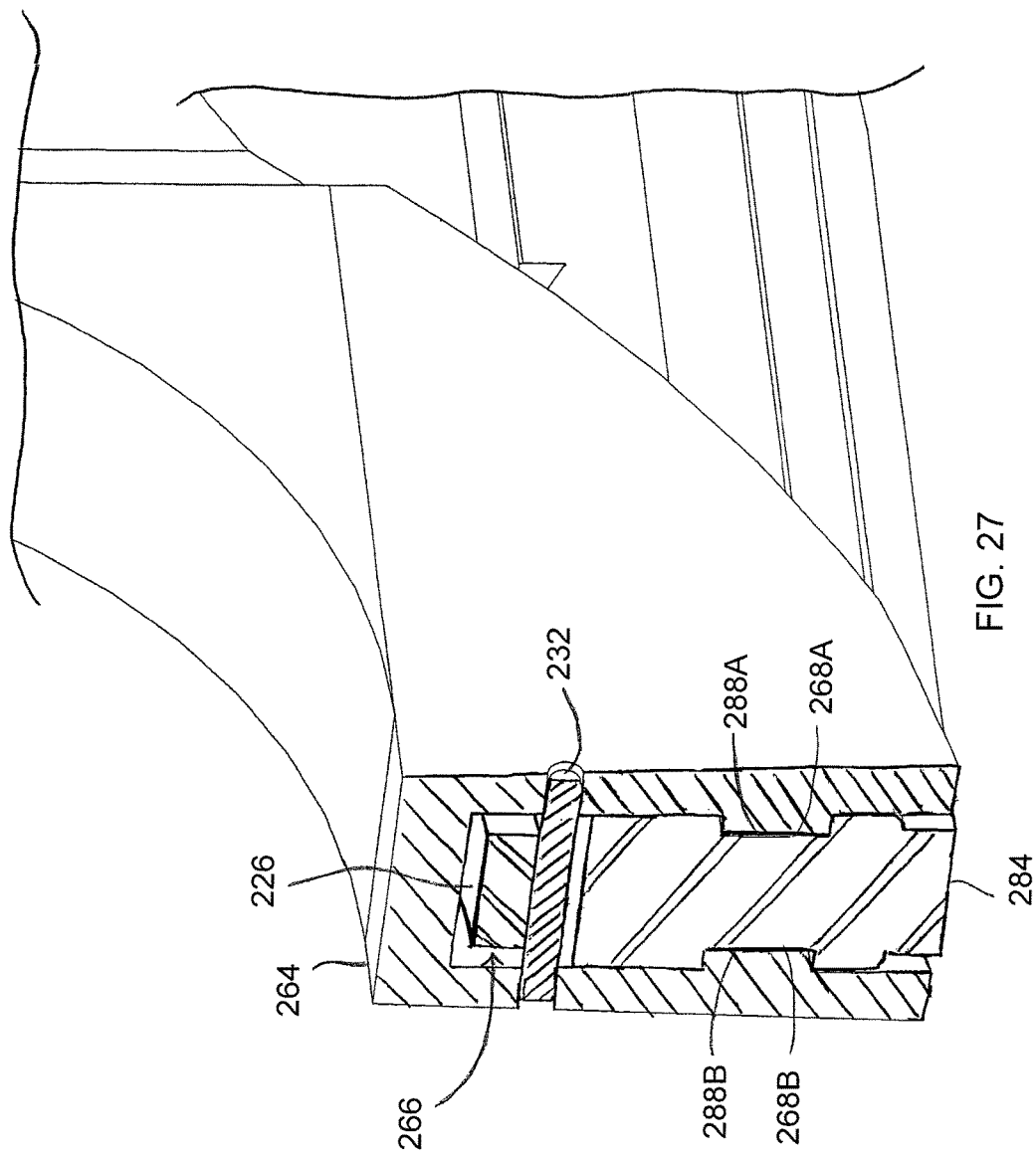

SKULL CLAMP OPENING APPARATUS AND METHOD

PRIORITY

This application claims priority to U.S. Provisional Patent Application Ser. No. 61/724,845, filed Nov. 9, 2012, entitled "SKULL CLAMP OPENING APPARATUS AND METHOD," and U.S. Provisional Patent Application Ser. No. 61/844,382, filed Jul. 9, 2013, entitled "SKULL CLAMP OPENING APPARATUS AND METHOD," the disclosures of which are incorporated by reference herein.

BACKGROUND

Head fixation devices are used in medical procedures where there is a need for stabilizing a patient's head and/or neck. One type of head fixation device used for such stabilization is a skull clamp. Skull clamps generally have a U-shape and are designed with pin holding devices at each upper end of the U-shape. The pin holding devices hold pins that engage with a patient's head to stabilize the patient's head and/or neck. With some skull clamps there are two adjustable arms that are selectively joined together to create the U-shape of the skull clamp. The adjustability of these arms is such that the skull clamp can be sized to fit patients having various head sizes. To facilitate applying and adjusting a skull clamp to a patient, some skull clamps include an opening device or locking and unlocking device, or release device.

While a variety of head fixation devices, and in particular skull clamps, have been made and used, it is believed that no one prior to the inventor has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements.

FIG. 1 depicts a perspective view of an exemplary skull clamp having an exemplary opening device showing a portion of an actuator in an open position.

FIG. 2 depicts a perspective view of the skull clamp of FIG. 1 with the opening device, and showing a portion of an actuator in a closed position.

FIG. 3A depicts a perspective view of a first arm of the skull clamp of FIG. 1, shown with the opening device and pin holder assembly removed.

FIG. 3B depicts a bottom cross section view of an attachment feature of the skull clamp of FIG. 1, taken along line 3B-3B shown in FIG. 3A.

FIG. 22 depicts a side view of the first arm and the opening device of the skull clamp or FIG. 10, shown with a portion of an actuator of the opening device in the open position.

FIG. 23 depicts a cross-sectional view of the first arm and the opening device of the skull clamp or FIG. 10, shown with a portion of an actuator of the opening device in the open position.

FIG. 24A depicts a side view of a second arm and the opening device of the skull clamp or FIG. 10, shown with the opening device engaged with the second arm.

FIG. 25 depicts a cross-sectional view of the skull clamp of FIG. 10 taken along line 25-25 of FIG. 10.

FIG. 26 depicts a cross-sectional view of the skull clamp of FIG. 10 taken along line 26-26 of FIG. 10.

FIG. 27 depicts a cross-sectional view of the skull clamp of FIG. 10 taken along line 27-27 of FIG. 10.

Figure 4:
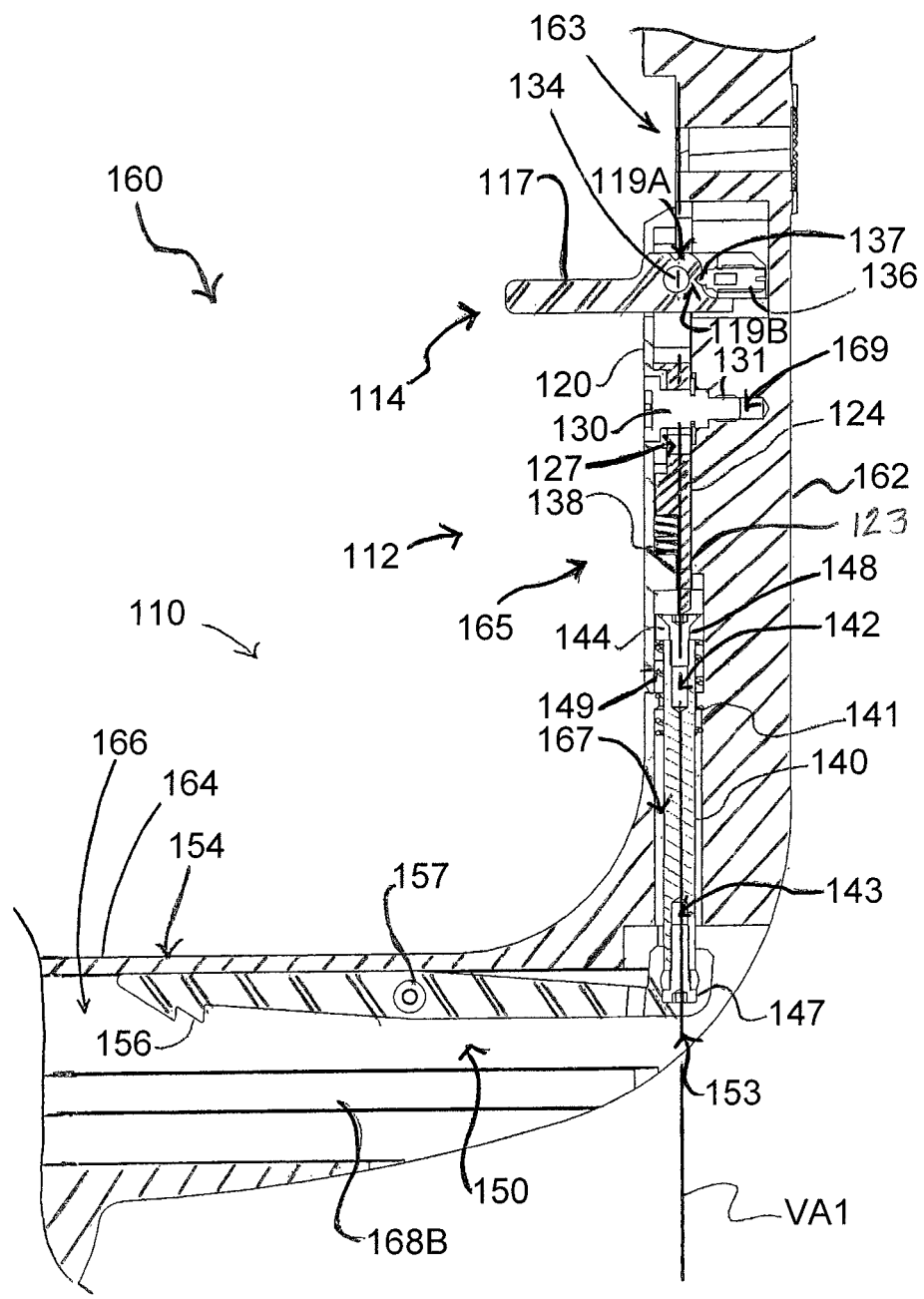
FIG. 4 depicts a side view, shown in cross section, of the first arm of the skull clamp of FIG. 1, showing the opening device in an opened position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description. As will be realized, the invention is capable of other different and obvious aspects, all without departing from the invention. Accordingly, the drawings and descriptions should be regarded as illustrative in nature and not restrictive.

I. First Exemplary Skull Clamp and Opening Device

FIGS. 1-2 illustrate an exemplary skull clamp (100) that incorporates an exemplary opening device (110). The skull clamp includes a first arm (160) and a second arm (180) that each include generally upright portions (162, 182) and generally lateral portions (164, 184). Lateral portion (184) of second arm (180) includes a plurality of teeth (186) positioned upward or toward where the patient's head would be positioned. Lateral portion (164) of first arm (160) includes a lateral slot (166), as best seen in FIG. 3A, that is configured to receive lateral portion (184) of second arm (180). Opening device (110) is substantially disposed within first arm (160). As will be discussed in more detail below, to achieve the desired alignment of arms (160, 180) when assembling them to form skull clamp (100), a pair of raised guides (168A, 168B) extend from each interior side surface of first arm (160) and engage with a pair of corresponding recessed slots (188A, 188B) formed in each exterior side of lateral portion (184) of second arm (180). As can be understood from FIGS. 4, 5, 8, and 9, opening device (110) functions to engage teeth (186) of second arm (180) to engage arms (160, 180) together in a selective locking fashion. These aspects will be described more fully below.

As shown in FIGS. 1-2, at a top of upright portions (162, 182) of each arm (160, 180) are pin holder assemblies (170, 190). On second arm (180), there is a single pin holder assembly (190) that holds a single pin (not shown). On first arm (160), there is a dual pin holder assembly (170) that holds two pins (not shown). As mentioned above, these pins engage with a patient's head to create the stabilization.

As shown in FIGS. 1-3B, skull clamp (100) also includes an attachment feature (172) that is located on lateral portion (164) of first arm (160). In the present example, attachment feature (172) is configured with first and second starbursts (171, 173). At one of starbursts (171, 173), is where skull clamp (100) can be attached to other structures, e.g., an operating table via one or more adapters. At the other one of starbursts (171, 173), other accessories can be attached to skull clamp (100), e.g., instrument holders, retractor devices, or other accessories that will be apparent to one of ordinary skill in the art in view of the teachings herein. In the present example, starbursts (171, 173) of attachment feature (172) are laterally offset from each other and are positioned in opposing directions. In this arrangement, threaded bores (175, 177) of respective starbursts (171, 173) are offset such that there is no overlap of bores (175, 177). With this configuration, attachment feature (172) can be sized smaller and have less mass compared to an attachment feature where the bores of the opposed facing starburst are aligned. In designs where the bores of the opposed facing starburst are aligned, the attachment feature must be sufficiently large such that if accessories attach to each starburst the threaded rods that connect with the threaded bores would not collide or interfere with one another. By using a configuration where starbursts (171, 173) are offset such that threaded bores (175, 177) are offset, the overall size and mass of attachment feature (172) can be reduced because the threaded rods of the accessories could not collide or interfere when accessories are attached with starbursts (171, 173) at the same time. In some other version, the offset may be vertically or diagonally instead of laterally.

Figure 5:
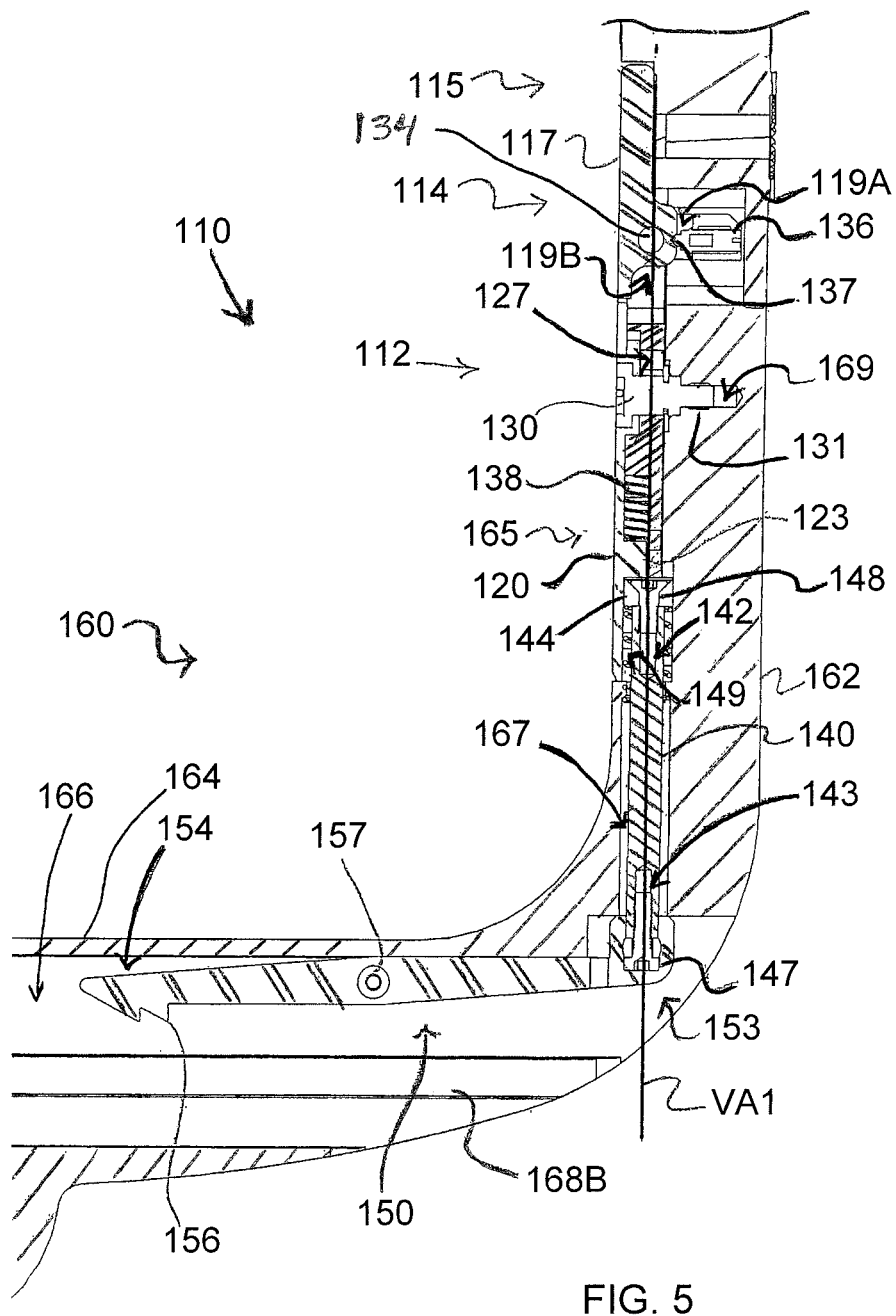
FIG. 5 depicts another side view, shown in cross section, of the first arm of the skull clamp of FIG. 1, showing the opening device in a closed position.
Figure 6:
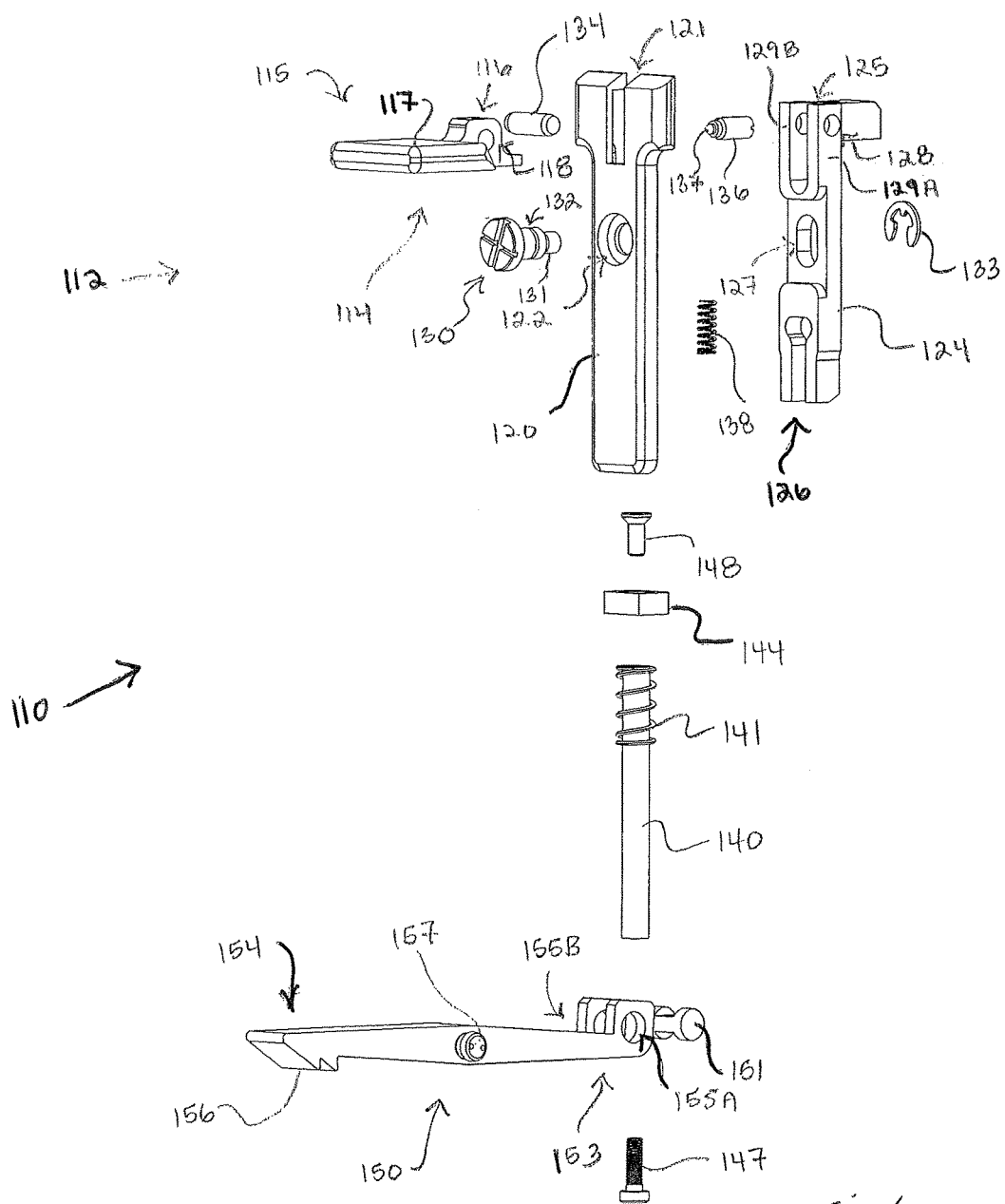
FIG. 6 depicts an exploded view, shown in perspective, of the opening device of FIG. 1.
Figure 7:
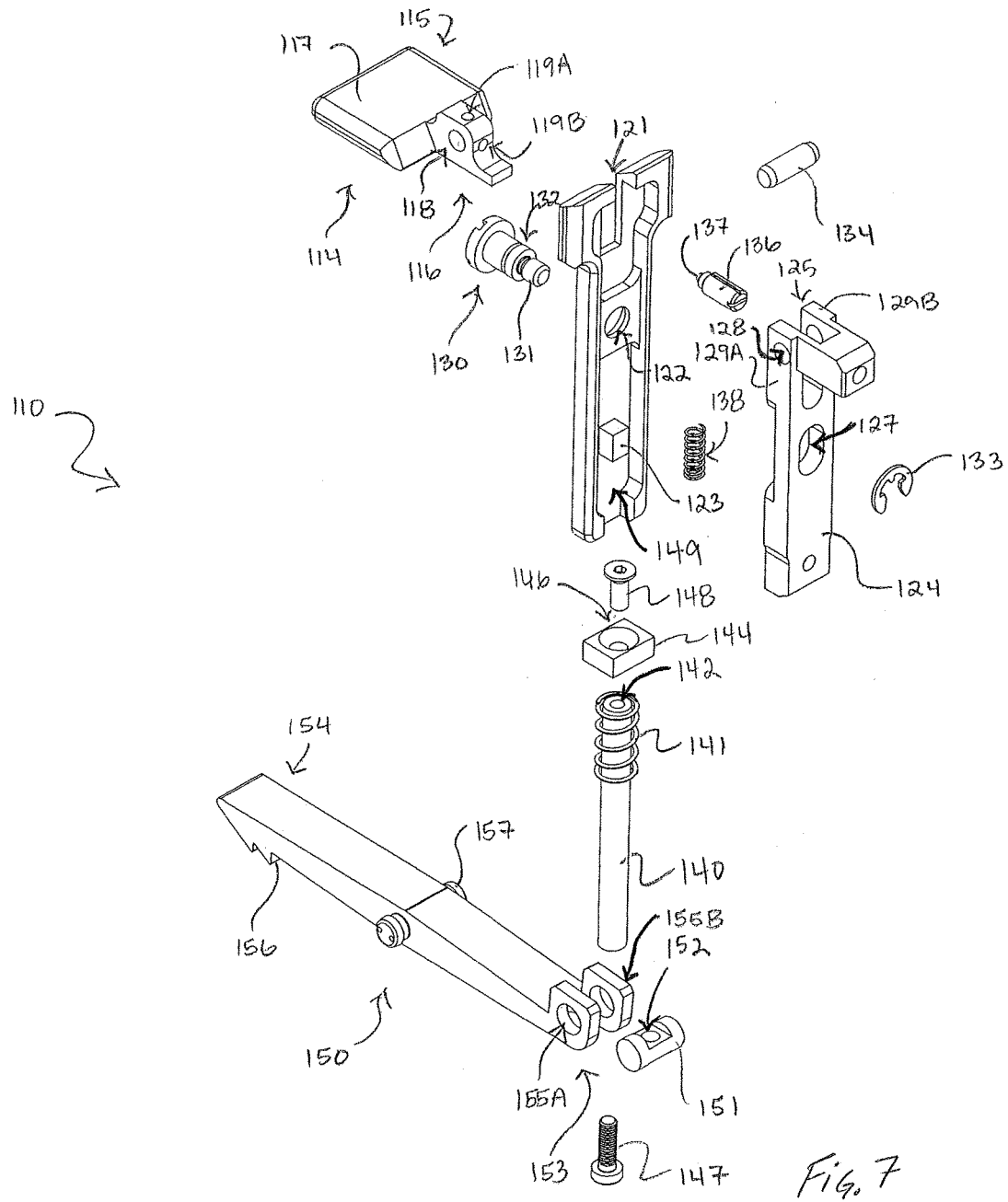
FIG. 7 depicts another exploded view, shown in perspective, of the opening device of FIG. 1.

FIGS. 4-5 illustrate a cross-sectional view of first arm (160) of skull clamp (100) including opening device (110). As also illustrated in FIGS. 6 and 7, opening device (110) comprises an actuator (112) positioned at a top of opening device (110). A trigger (117) of actuator (112) extends away from upright portion (162) of first arm (160) when actuator (112) is in an open position. Trigger (117) is positionable to fit within a recessed space (163) formed within first arm (160) when actuator (112) is in a closed position. When actuator (112) is in the open position, trigger (117) is readily accessible to a user such that opening device (110) can be operated to open and/or adjust skull clamp (100). This opening or adjustment allows for changing the relative position of arms (160, 180) with respect to one another. When actuator (112) is in the closed position and with trigger (117) positioned within recessed space (163), trigger (117) is not readily accessible to a user such that opening device (110) cannot be operated to open and/or adjust skull clamp (100). The secure retention of trigger (117) within recessed space (163) acts as a safety such that actuator (112), and hence opening device (110), cannot be inadvertently operated. As shown in the illustrated version, opening device (110) is actuated or able to be actuated to open, close, or adjust skull clamp (100) from a location along upright portion (162) of first arm (160) of skull clamp (100), and more specifically from a location near, proximate, or just below pin holder assembly (170) along upright portion (162). In some versions a proximate distance between trigger (117) of actuator and pin holder assembly (170) is less than 10 centimeters. In some other versions this distance is less than 7.5 centimeters. Still in some other versions this distance is less than 5 centimeters.

FIGS. 3-5 illustrate a space defined within first arm (160) in which opening device (110) is slidably and rotatably disposed. Lateral slot (166) of first arm (160) extends and joins with an upright opening (167) that extends along a lower portion of upright portion (162) of first arm (160). Upright opening (167) defines a vertical axis (VA1) parallel to upright portion (162) of first arm (160). A recess (165) is formed in the surface of upright portion (162) of first arm (160). Upright opening (167) extends and joins with recess (165). Upright opening (167), lateral slot (166), and recess (165) effectively define the space within which opening device (110) is disposed.

As shown in FIGS. 4-7, opening device (110) comprises actuator (112), a rod (140) and a lever (150). Actuator (112) comprises a first member (114), a second member (120), a third member (124), pins (134, 136), screw (130), and spring (138). First member (114) comprises a first portion (115) and a second portion (116). First portion (115) of first member (114) comprises a trigger (117) as described above. Second portion (116) of first member (114) comprises an opening (118). Second member (120) of actuator (112) includes a longitudinal slot (121) and an opening (122). Third member (124) of actuator (112) includes a pair of longitudinal slots (125, 126), a longitudinal opening (127), and a transverse opening (128) formed in a pair of walls (129A, 129B) which define longitudinal slot (125). A tip of screw (130) presents a threaded portion (131). As shown in FIGS. 3-5, recess (165) of first arm (160) presents a threaded bore (169). Screw (130) passes through opening (122) of second member (120), then through longitudinal opening (127) of third member (124), and then matingly threads into threaded bore (169) such that second member (120) is statically coupled relative to first arm (160) whereas third member (124) is slidably coupled between second member (120) and the first arm (160). In this position, third member (124) is slidable in a direction generally parallel with the vertical axis (VA1) defined by upright opening (167) from an upward position to a downward position. A clip (133) may be secured between third member (124) and the surface of recess (165) of first arm (160) within an annular channel (132) formed in an exterior of screw (130) to better secure third member (124) relative to second member (120) and first arm (160).

As shown in FIGS. 6-7, second member (120) further comprises a projection (123). When second member (120) and third member (124) are assembled, projection (123) is disposed within longitudinal slot (126) of third member (124). Spring (138) is positioned within longitudinal slot (126) of third member (124) between a top surface of longitudinal slot (126) and projection (123) of second member (120). Spring (138) bears against the top surface of longitudinal slot (126) such that third member (124) is biased toward the upward position.

Second member (120) and third member (124) are assembled such that longitudinal slot (121) of second member (120) and longitudinal slot (125) of third member (124) are substantially aligned at a top of actuator (112). Second portion (116) of first member (114) is slidably and rotatably disposed within longitudinal slot (121) of second member (120) and rotatably disposed within longitudinal slot (125) of third member (124). Pin (134) passes through opening (128) in walls (129A, 129B) of third member (124) and opening (118) of first member (114) within longitudinal slot (125) of third member (124) such that first member (114) and third member (124) are rotatably coupled together. Therefore, first member (114) is selectively rotatable about pin (134) within longitudinal slots (121, 125) from the closed position to the opened position and vice versa. As will be discussed in more detail below, this rotatability allows first member (114) to be positioned in the two positions described above for operating and securing opening device (110). Also, downward movement of first member (114) within longitudinal slot (121), and in particular trigger (117), will cause downward movement of third member (124).

Pin (136) comprises a resilient tip (137). Pin (136) is threaded into third member (124) such that pin (136) and resilient tip (137) extend inwardly into longitudinal slot (125) of third member (124). Second portion (116) of first member (114) presents a pair of detents (119A, 119B) configured to receive and engage resilient tip (137) of pin (136) to selectively secured first member (114) in a particular position. A first detent (119A) coincides with the closed position such that when first member (114) is rotated into the closed position, resilient tip (137) is received within first detent (119A). A second detent (119B) coincides with the open position such that when first member (114) is rotated into the open position, resilient tip (137) is received within second detent (119B). Therefore, as first member (114) rotates within longitudinal slots (121, 125), resilient tip (137) of pin (136) will engage detents (119A, 119B) to selectively secure first member (114) in the closed position and in the open position.

As best seen in FIGS. 4-5, rod (140) is slidably disposed within recess (165) and upright opening (167) such that rod (140) is slidable relative to vertical axis (VA1) from an upward position to a downward position. A top surface of rod (140) presents a threaded bore (142). Engagement member (144) comprises an opening (146). Screw (148) passes through opening (146) of engagement member (144) and threads into threaded bore (142) of rod (140) such that rod (140) and engagement member (144) are coupled together. Engagement member (144) is slidably disposed within a space defined by a recess (149) formed in second member (120) and recess (165) of first arm (160). A bottom edge of third member (124) contacts a top surface of engagement member (144). Thus, as third member (124) is moved downward, rod (140) will be driven downward as well. A spring (141) is disposed about rod (140) and positioned between a bottom surface of engagement member (144) and a bottom surface of recess (165) about the opening of upright opening (167) such that spring (141) bears against the bottom surface of engagement member (144) such that engagement member (144) and rod (140) are biased toward the upward position. This upward bias will cause the bottom edge of third member (124) to remain in contact with the top surface of engagement member (144). Upward movement of engagement member (144) is limited by projection (123).

At a base of rod (140), rod (140) couples with lever (150). In particular, a bottom surface of rod (140) presents a threaded bore (143). Pin (151) comprises an opening (152) formed in symmetric flat surfaces of pin (151). Screw (147) passes through opening (152) of pin (151) and threads into threaded bore (143) of rod (140) such that rod (140) and pin (151) are coupled together. Ends of pin (151) are disposed within a pair of openings (155A, 155B) formed within a first end (153) of lever (150). Therefore, as rod (140) is driven downward or upward, first end (153) of lever (150) will be driven respectively downward or upward as well.

As can be best understood from FIGS. 4-5, when assembled, lever (150) is rotatably coupled within lateral slot (166) of first arm (160) via a pin (157) disposed within a pair of bores (174) formed within an interior of lateral slot (166) of first arm (160). Pin (157) creates a pivoting axis about which lever (150) can rotate such that lever (150) is rotatable about pin (157) within slot (166). A second end (154) of lever (150) comprises teeth (156) positioned downward or away from where the patient's head would be positioned. Teeth (156) are operable to engage teeth (186) of second arm (180). First end (153) and second end (154) are disposed on opposite ends of lever (150) about pin (157) such that as first end (153) of lever (150) is driven downward, second end (154) of lever (150) is driven upward, and such that as first end (153) of lever (150) is driven upward, second end (154) of lever (150) is driven downward.

Figure 8:
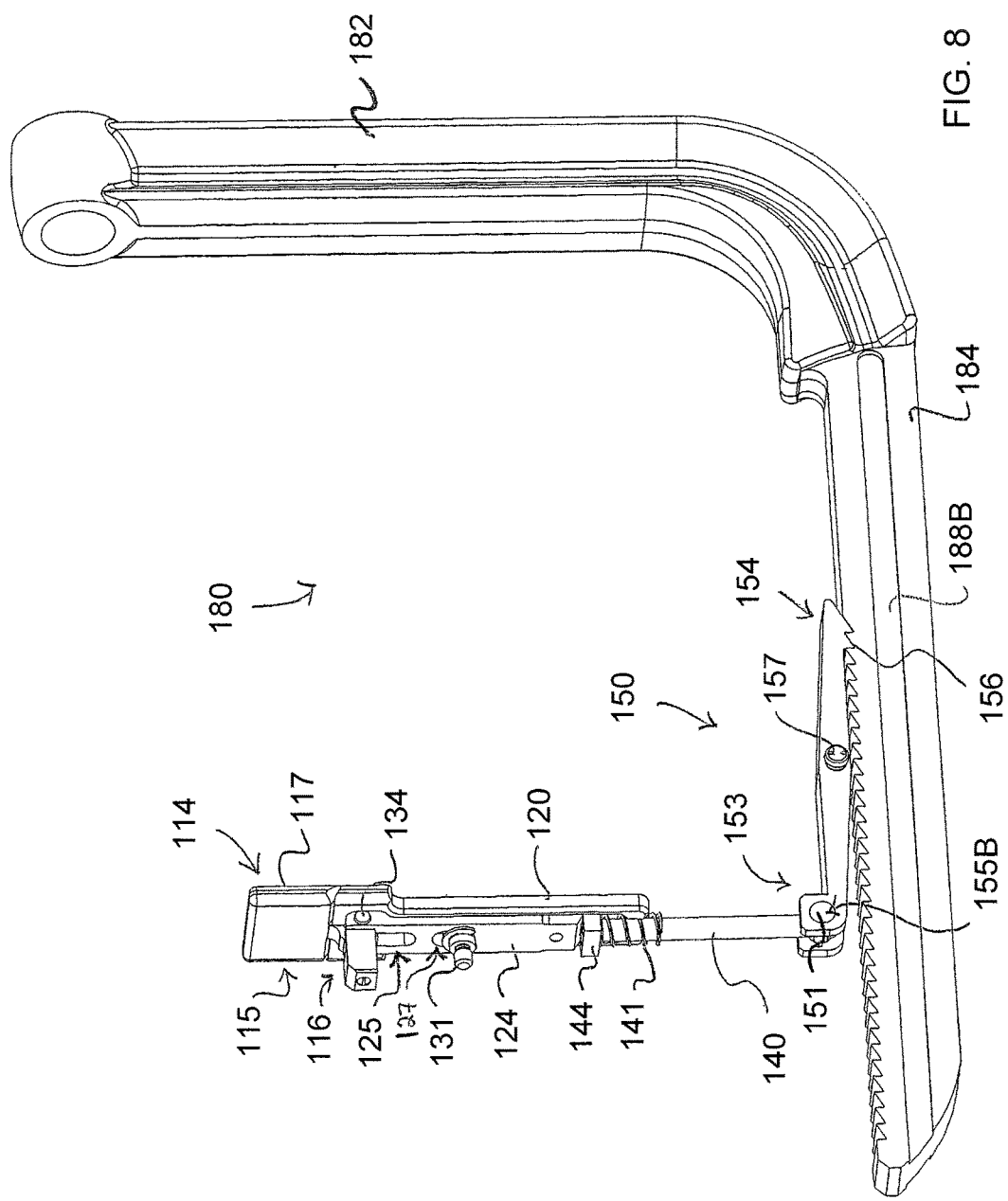
FIG. 8 depicts a perspective view of a second arm of the skull clamp of FIG. 1, shown engaged with the opening device.
Figure 9:
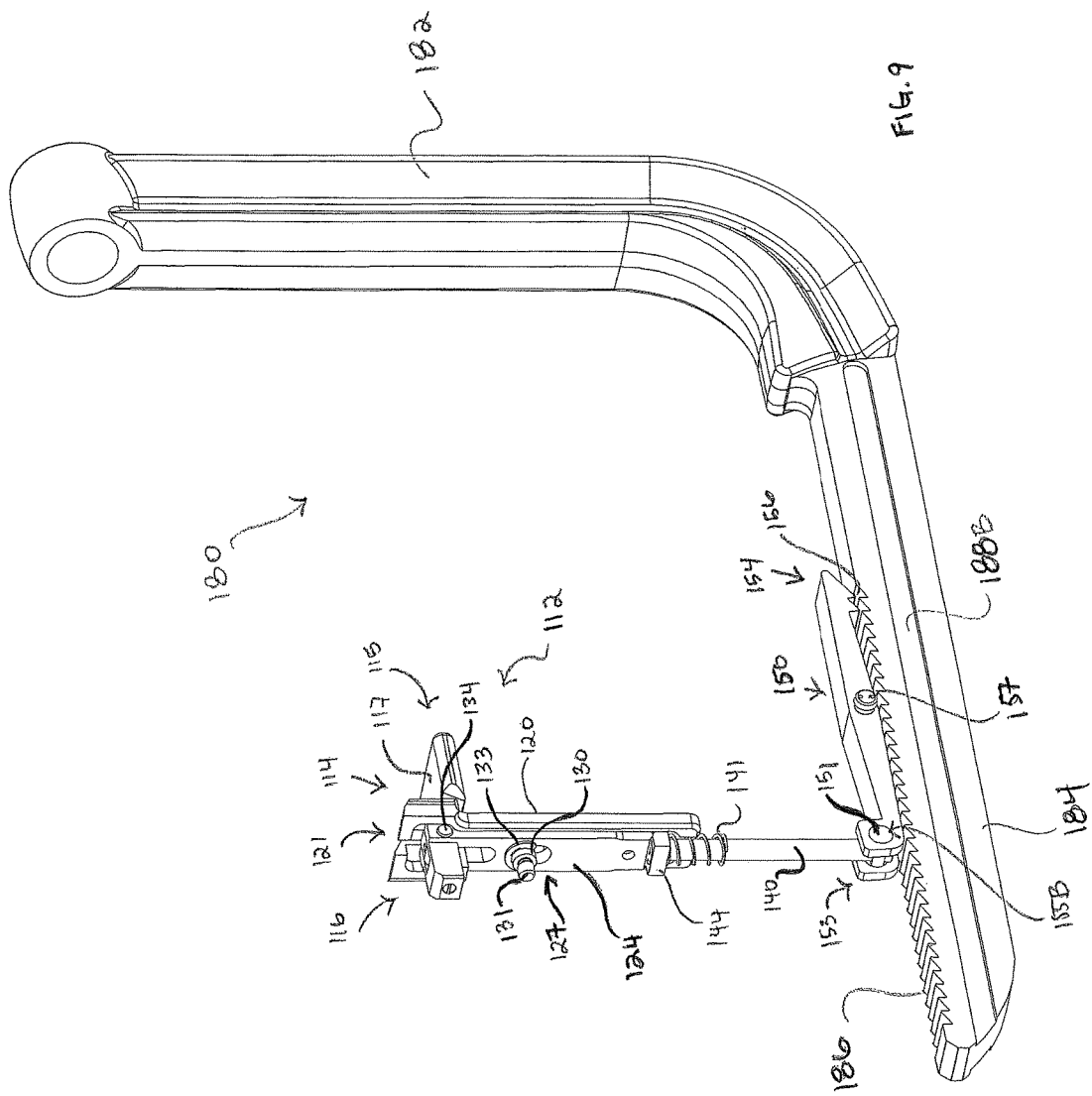
FIG. 9 depicts another perspective view of the second arm of the skull clamp of FIG. 1, shown disengaged from the opening device.

FIGS. 8 and 9 illustrate other views that further show features and operability of opening device (110). FIG. 8 illustrates a view with first arm (160) not shown to reveal how opening device (110) engages with teeth (186) of second arm (180). In FIG. 8, opening device (110) is engaged with teeth (186) such that the arms (160, 180) cannot be moved relative to one another. FIG. 9 illustrates a similar view, but with opening device (110) not engaged with teeth (186) such that the arms (160, 180) can be moved relative to one another. To accomplish such movement, a user would first rotate trigger (117) of actuator (112) of opening device (110) downward to remove it from the closed position and into the open position such that trigger (117) is readily accessible. Then a user can push downward on trigger (117). This downward motion causes rod (140) to move downward as well. With the connection of rod (140) to lever (150), and with pin (157) and bores (174) that define the pivoting axis, first end (153) of lever (150) moves downward, while second end (154) of lever (150) moves upward. The upward motion of second end (154) of lever (150) carries teeth (156) upward as well, and away from teeth (186) of second arm (180) to the point where teeth (156) of lever (150) disengage from teeth (186) of second arm (180). With such disengagement, arms (160, 180) can be adjusted relative to one another, either opening or closing skull clamp (100). When adjustment is complete, the user can remove the downward force applied to trigger (117) and opening device (110) will go through the reverse motion. Spring (141) imparts an upward bias upon the engagement member (144) thus driving third member (124), rod (140), and consequently first end (153) of lever (150) upward. Also, spring (138) imparts an upward bias upon third member (124). This driving upward of first end (153) of lever (150) causes second end (154) and teeth (156) of lever (150) to be driven downward thus engaging teeth (186) of second arm (180). With such engagement, arms (160, 180) cannot be adjusted to a larger position relative to one another.

In one exemplary use of skull clamp (100), a single user can open or adjust skull clamp (100) without being aided by another person. For instance, a user grasps upright portions (162, 182) of each arm (160, 180) with their hands. With this position, the user can use a thumb to rotate trigger (117) of actuator (112) of opening device (110) downward so that opening device (110) is operable. At this point, the user can use the thumb to apply a downward force or pressure to trigger (117) of opening device (110). As described above, this action causes teeth (156) of lever (150) to disengage teeth (186) of second arm (180). At this point the user can apply outward force or pressure on arms (160, 180) to increase the distance between arms (160, 180) to either fully open skull clamp (100) or adjust skull clamp (100) to a larger position or size. The user could also close skull clamp (100) or adjust skull clamp (100) to a smaller position or size using this process. However, rotating and depressing trigger (117) is not required in all versions to close skull clamp (100) or adjust skull clamp (100) to a smaller position or size. Once skull clamp (100) is at the desired position or size, the user releases the downward force on trigger (117) and teeth (156) of lever (150) engage teeth (186) of second arm (180) again to secure arms (160, 180) from further movement.

In the present version of skull clamp (100), but not required in all versions, the orientation of teeth (186) of second arm (180) and teeth (156) of lever (150) permit a user to move arms (160, 180) closer together without the need to rotate trigger (117) of actuator (112) to its folded-down or open position and depress trigger (117). In the present example, the orientation and slope of teeth (156, 186), and the contact between teeth (156, 186), drive second end (154) of lever (150) upward as arms (160, 180) are moved closer together. This is so even without rotating trigger (117) of actuator (112) to its folded-down or open position and depress trigger (117). This movement of arms (160, 180) closer together disengages teeth (156) of lever (150) from teeth (186) of second arm (180) sufficiently such that skull clamp (100) can be made smaller (i.e. the space between upright portions (162, 182) of arms (160, 180) become closer as skull clamp (100) gets smaller). Furthermore, spring (138) and spring (141) bias second end (154) of lever (150) downward so that teeth (156, 186) engage unless the spring biases are sufficiently overcome by a user either repositioning arms (160, 180) to a closer arrangement as described above or depressing trigger (117) of actuator (112) as also described further above. In view of the teachings herein, it will be appreciated that in some versions of skull clamp (100), teeth (186) and teeth (156) and/or other features may be configured such that a user must depress trigger (117) of actuator (112) of opening device (110) to move arms (160, 180) closer together.

Skull clamp (100) can be cleaned and/or sterilized between uses. In view of the teachings herein, the various types of cleaning and sterilization suitable for use with skull clamp (100) will be apparent to those of ordinary skill in the art. In the present example, certain components can be removed from skull clamp (100) to improve or enhance cleaning and the ease with which cleaning is accomplished. For instance, pin holder assemblies (170, 190) are removable for cleaning. Also, first arm (160) and second arm (180) can be disassembled as described above for thorough cleaning. Also in the present example, second member (120) can be removed from first arm (160) by removing screw (130) when cleaning or sterilizing skull clamp (100). Although not required in all versions, in some versions, in addition to second member (120) being removable for cleaning, third member (124), and connected first member (114) may also be removed from first arm (160) for cleaning. Still in other versions third member (124) and connected first member (114) remain connected with skull clamp (100) even when second member (120) is removed for cleaning and/or sterilization.

II. Second Exemplary Skull Clamp and Opening Device

Figure 10:
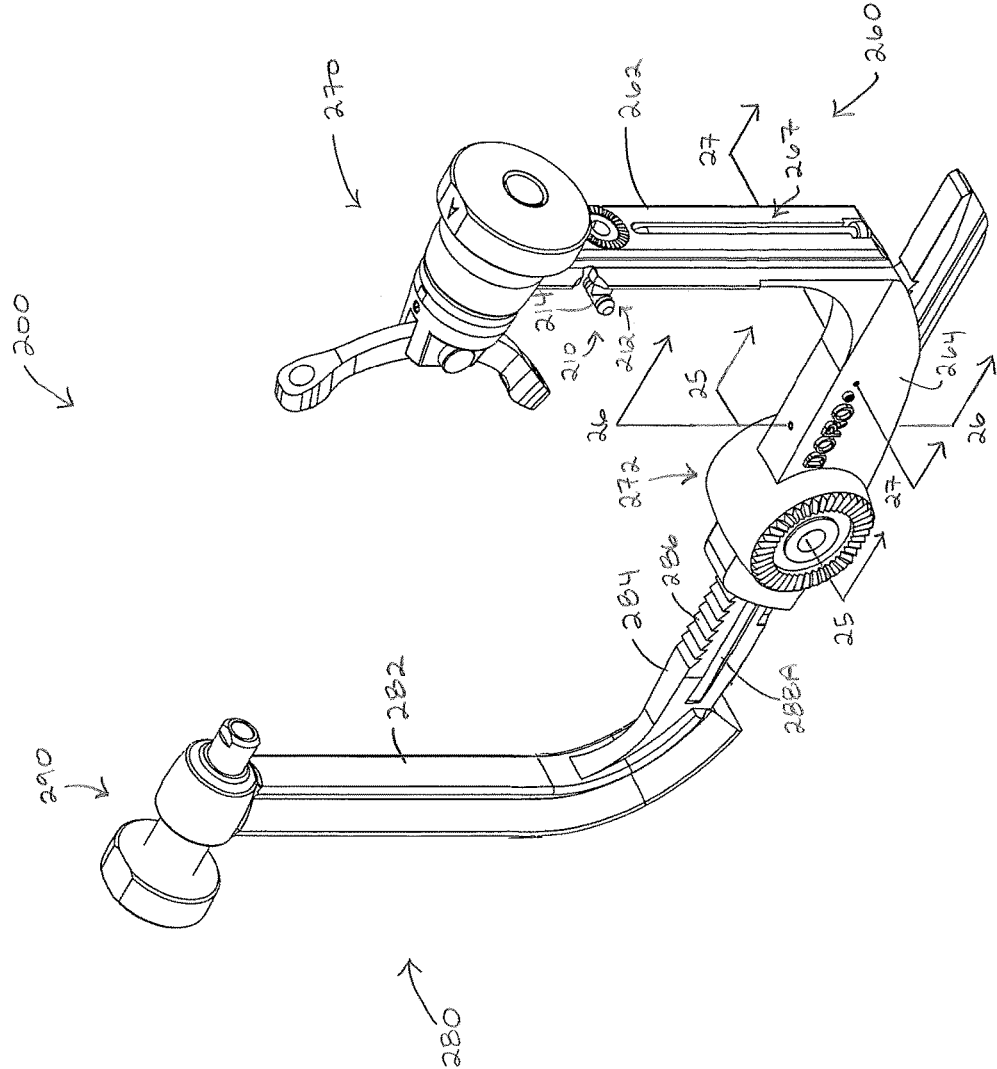
FIG. 10 depicts a perspective view of an exemplary alternative skull clamp having an exemplary opening device showing a portion of an actuator in an open position.
Figure 13:
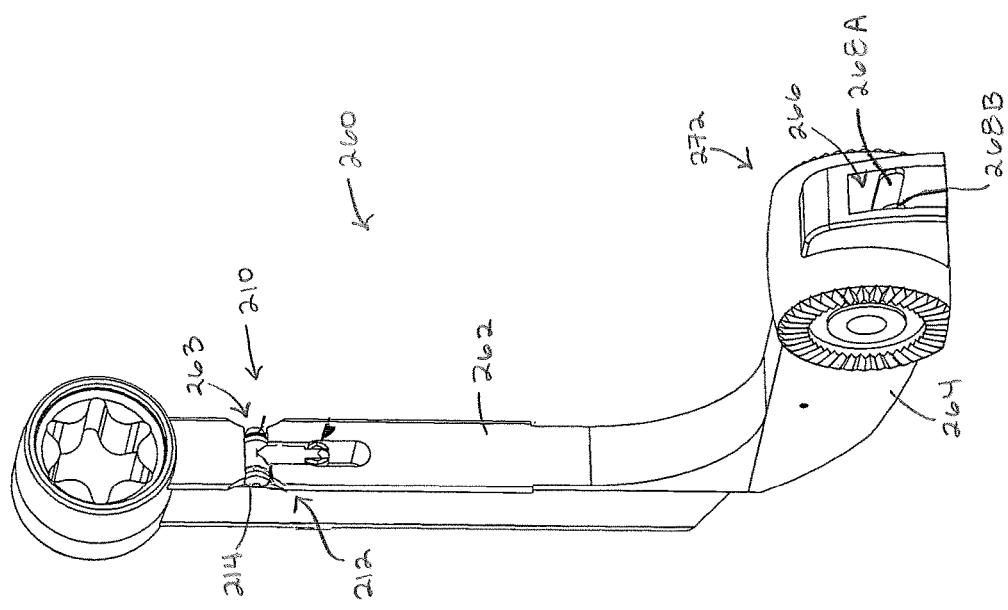
FIG. 13 depicts a perspective view of a first arm and the opening device of the skull clamp of FIG. 10, shown with a portion of an actuator of the opening device in a closed position.

FIG. 10 illustrates an exemplary skull clamp (200) that incorporates an exemplary opening device (210). Skull clamp (200) includes a first arm (260) and a second arm (280) that each include generally upright portions (262, 282) and generally lateral portions (264, 284). Lateral portion (284) of second arm (280) includes a plurality of teeth (286) positioned upward or toward where the patient's head would be positioned. Lateral portion (264) of first arm (260) includes a lateral slot (266), as best seen in FIG. 13, that is configured to receive lateral portion (284) of second arm (280). Opening device (210) is substantially disposed within first arm (260). As will be discussed in more detail below, to achieve the desired alignment of arms (260, 280) when assembling them to form skull clamp (200), a pair of raised guides (268A, 268B) extend from each interior side surface of first arm (260) and engage with a pair of corresponding recessed slots (288A, 288B) formed in each exterior side of lateral portion (284) of second arm (280). As can be understood from FIGS. 23-24B, opening device (281) functions to engage teeth (286) of second arm (280) to engage arms (260, 280) together in a selective locking fashion. These aspects will be described more fully below.

As shown in FIG. 10, at a top of upright portions (262, 282) of each arm (260, 280) are pin holder assemblies (270, 290). On second arm (280), there is a single pin holder assembly (290) that holds a single pin (not shown). On first arm (260), there is a dual pin holder assembly (270) that holds two pins (not shown). As mentioned above, these pins engage with a patient's head to create the stabilization.

Figure 11:
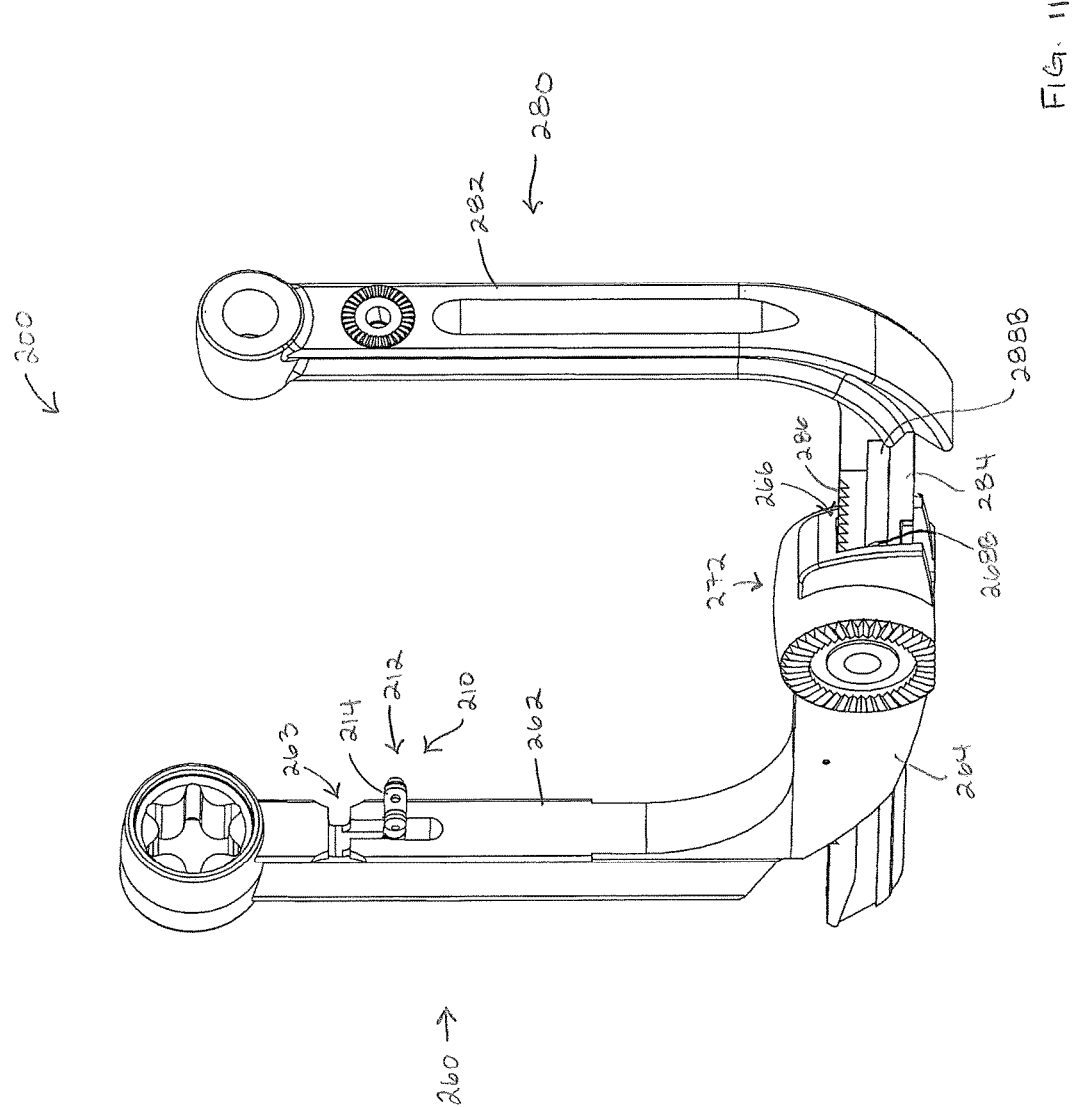
FIG. 11 depicts another perspective view of the skull clamp or FIG. 10, shown with the opening device, and showing a portion of an actuator in the open position.
Figure 12:
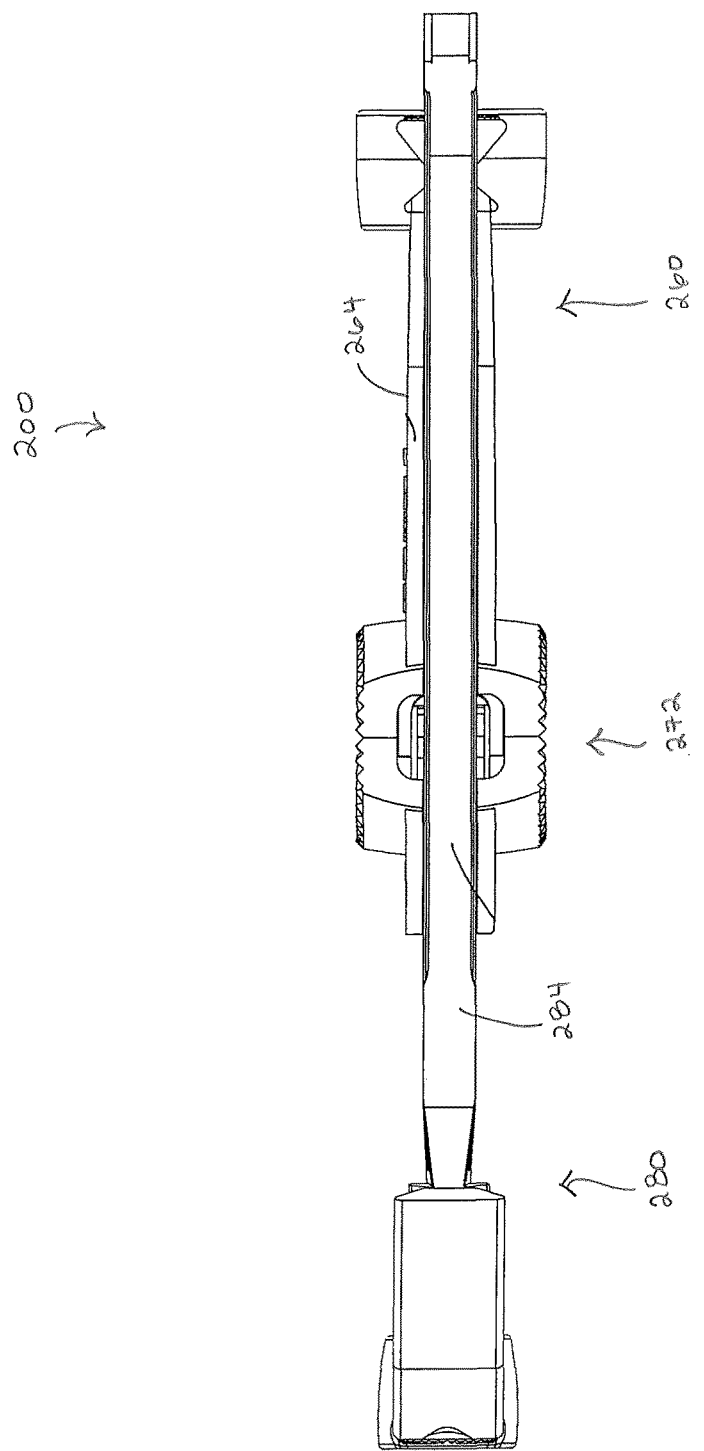
FIG. 12 depicts a bottom view of the skull clamp or FIG. 10.

As shown in FIGS. 10-12, skull clamp (200) also includes an attachment feature (272) that is located on lateral portion (264) of first arm (260). In the present example, attachment feature (272) is configured as a starburst and this is where skull clamp (200) can be attached to other structures, e.g., an operating table via one or more adapters.

FIG. 12 illustrates a bottom view of skull clamp (200). In this version, lateral slot (266) of first arm (260) is open on the bottom side and second arm (280) is viewable from the bottom. In some other versions, lateral slot (266) of first arm (260) can be partially or fully closed. As also shown in FIG. 12, among other figures, the bottom side of the assembled skull clamp (200) is substantially smooth, or flat, with no projection extending downward from the bottom side.

As partially shown in FIG. 11, opening device (210) of skull clamp (200) includes an actuator (212) positioned at a top of opening device (210) and within upright portion (262) of first arm (260). Thus, skull clamp (200) includes opening device (210) that is actuated or able to be actuated to open, close, or adjust skull clamp (200) from a location along upright portion (262) of first arm (260) of skull clamp (200), and more specifically from a location near or just below pin holder assembly (270) along upright portion (262). A trigger (214) of actuator (212) is configured to pivot between an open position and a closed position. In FIG. 11, trigger (214) of actuator (212) of opening device (210) extends away from upright portion (262) of first arm (260) when actuator (212) is in the open position. As shown in FIG. 13, trigger (214) of actuator (212) of opening device (210) is configured to fit within a recessed space (263) formed within an interior surface of upright portion (262) of first arm (260) when trigger (214) is in the closed position. When trigger (214) of actuator (212) is in the open position, trigger (214) is readily accessible to a user such that opening device (210) can be operated to open and/or adjust skull clamp (200). This opening or adjustment allows for changing the relative position of arms (260, 280) with respect to one another. When trigger (214) of actuator (212) is in the closed position and trigger (214) positioned within recessed space (263), trigger (214) is inaccessible to a user and thus opening device (210) cannot be operated to open and/or adjust skull clamp (200) to a larger size. Also, in the closed position, trigger (214) is securely retained within recessed space (263) by contact between one or more o-rings (215, 216) positioned about a first member (218) of trigger (214) and one or more portions of recessed space (263) of first arm (260). This secure retention of trigger (214) within recessed space (263) acts as a safety such that actuator (212), and hence opening device (210), cannot be inadvertently operated.

Figure 14:
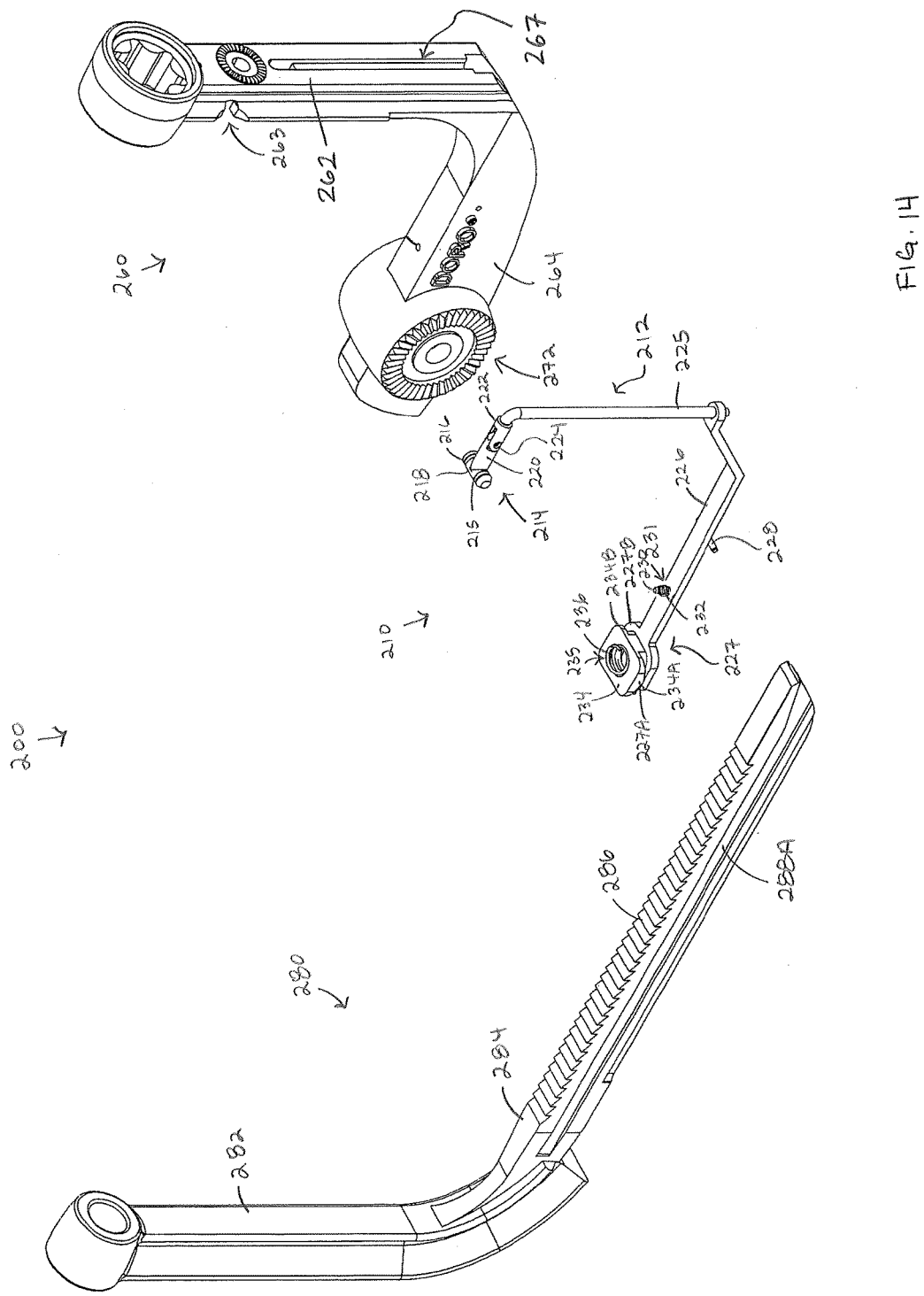
FIG. 14 depicts a partially exploded perspective view of the skull clamp of FIG. 10.

FIG. 14 illustrates a partially exploded view of certain components of skull clamp (200), namely first arm (260), second arm (280), and opening device (210). As understood from FIG. 14, in conjunction with other views, opening device (210) fits within a space defined within first arm (260). Lateral slot (266) of first arm (260) extends and joins with a bottom portion of an upright slot (267) that is formed within an exterior surface of upright portion (262) of first arm (260) along a lower portion of upright portion (262) of first arm (260). As shown in FIG. 23, a lateral opening (269) passes through upright portion (262) of first arm (260) and connects a top portion of upright slot (267) formed in the exterior surface of upright portion (262) of first arm (260) with recessed space (263) formed within the interior surface of upright portion (262) of first arm (260). Upright slot (267) defines a vertical axis (VA2) parallel to upright portion (262) of first arm (260). Lateral slot (266), upright slot (267), lateral opening (269), and recessed space (263) effectively define the space within which opening device (210) is disposed. FIG. 23 includes an illustration of a cross section view of first arm (260) that illustrates this space and opening device (210) positioned within.

Figure 21:
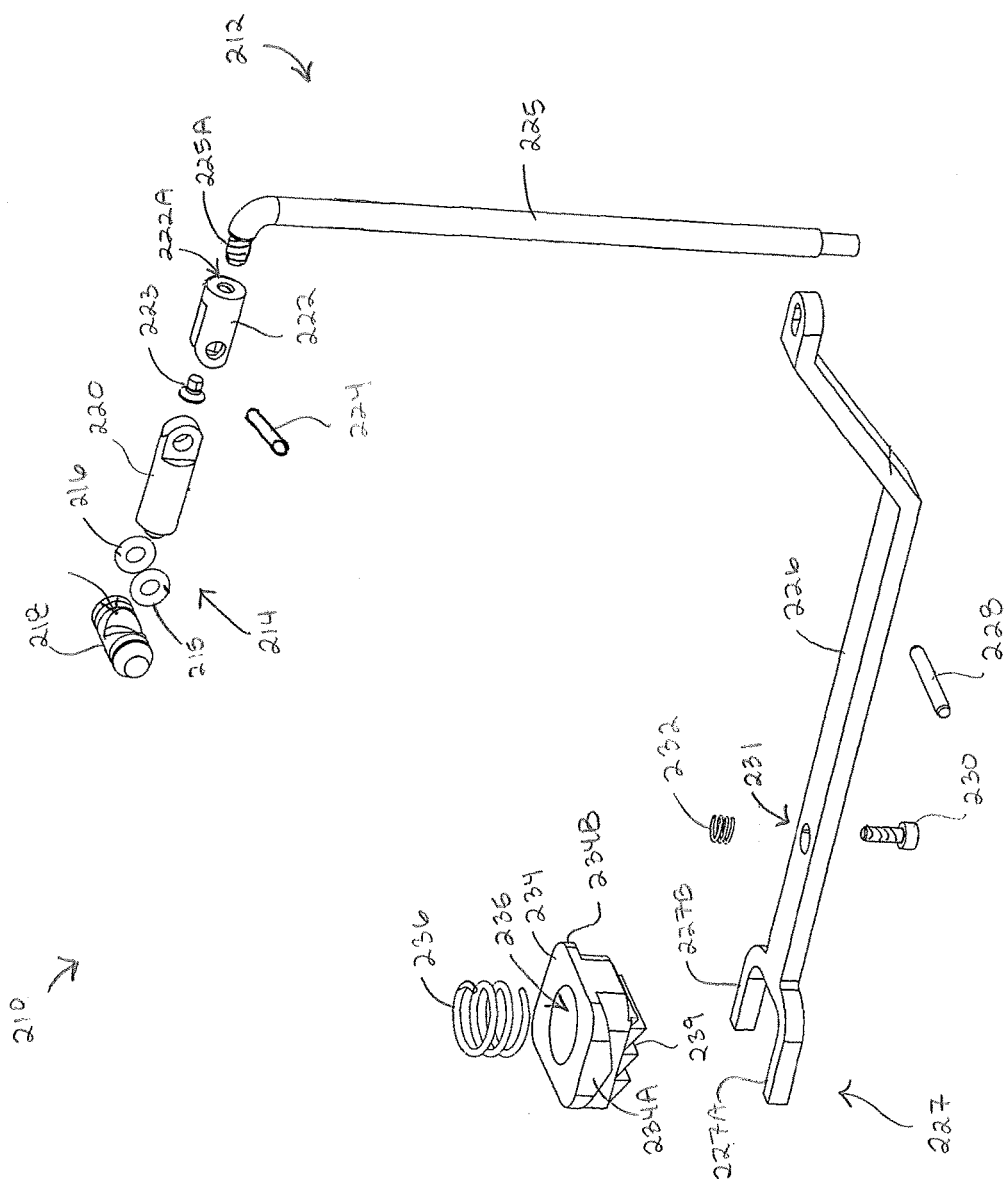
FIG. 21 depicts an exploded perspective view of the opening device of FIG. 10.

FIGS. 15-20 illustrate other views of opening device (210), and FIG. 21 illustrates an exploded view of opening device (210). As seen from these views, opening device (210) comprises actuator (212), a lever (226), a pair of springs (232, 236), a screw (230), a pin (228), and a locking member (234).

Actuator (212) comprises trigger (214) and a rod (225). Trigger (214) comprises a first member (218), a second member (220), a third member (222), pair of o-rings (215, 216), a screw (223), and a pin (224). Rod (225) is slidably disposed within upright slot (267) such that rod (225) is vertically translatable between an upward position and a downward position. An upper portion of rod (225) extends into lateral opening (269). Third member (222) of trigger (214) is disposed within lateral opening (269) of first arm (260). Third member (222) includes a threaded bore (222A) that is configured to threadably engage threads (225A) located on an upper portion of rod (225). Threads (225A) of the upper portion of rod (225) also include a threaded bore (225B) that is configured to receive screw (223). Screw (223) extends through threaded bore (222A) of third member (222) to prevent third member (222) from becoming disconnected from rod (225). Second member (220) is configured such that it can be rotated about an axis defined by pin (224). With the threaded engagement between third member (222) and rod (225), the upper end of rod (225) translates laterally in response to rotation of second member (220). As shown in FIG. 22, this lateral translation of rod (225) creates more unoccupied space within upright slot (267) of first arm (260) to help when cleaning and sterilizing skull clamp (200) and its components.

Figure 15:
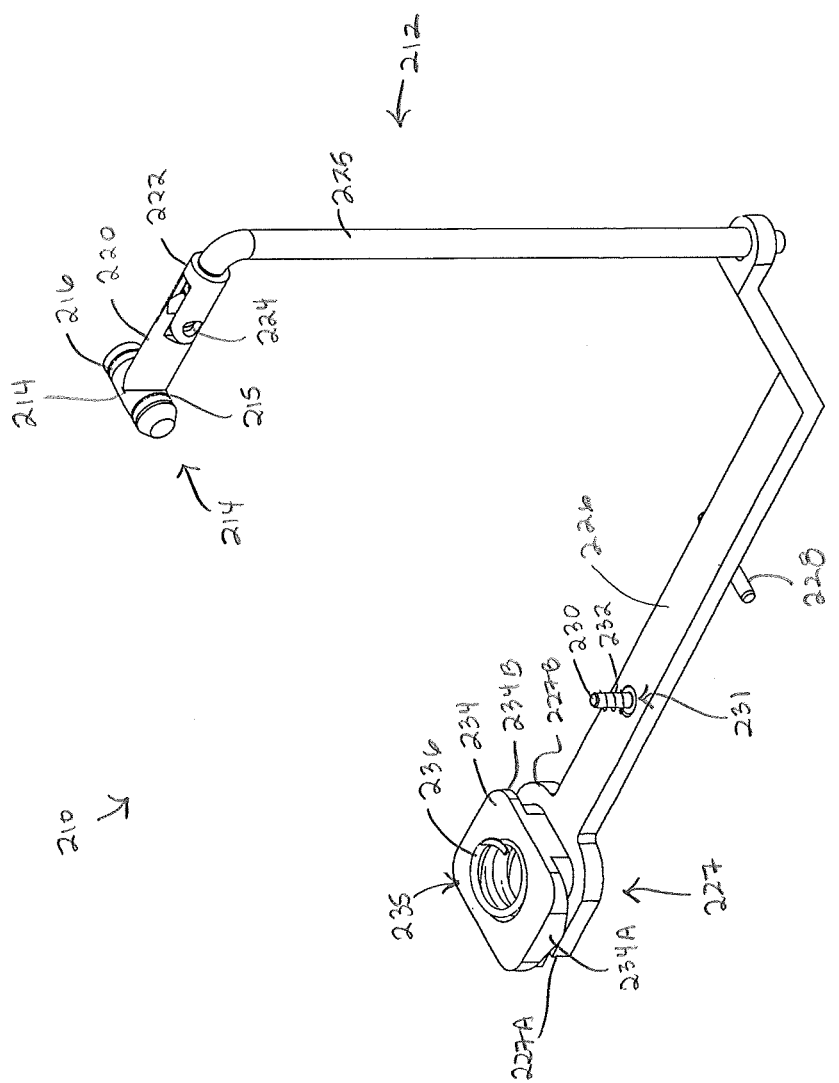
FIG. 15 depicts a perspective view of the opening device of FIG. 10.

First member (218) of trigger (214) is connected with second member (220). O-rings (215, 216) are positioned about portions of first member (218) such that, as described above, o-rings (215, 216) contact portions of recessed space (263) of first arm (260) when trigger (214) is in the closed position to retain trigger (214) in the safety position or stored position. Second member (220) is pivotably coupled with third member (222) via pin (224) such that second member (220) rotates about pin (224) relative to third member (222). This pivot connection allows trigger (214) to be positioned in the open position and closed position as described above for operating and securing opening device (210). It should be understood that the rotation of trigger (214) may be limited such that when trigger (214) is in the open position, trigger (214) is in a substantially horizontal orientation as shown in FIG. 15. Because of the threaded engagement between third member (222) and rod (225), it should be understood that vertical translation of trigger (214) will cause vertical translation of rod (225) within upright slot (267) between the upward position and the downward position.

At a base of rod (225), rod (225) connects with a first end of lever (226) such that vertical translation of rod (225) causes vertical translation of the first end of lever (226) and such that vertical translation of the first end of lever (226) causes vertical translation of rod (225). A second end of lever (226) comprises a two-prong member (227). Two-prong member (227) comprises a first prong (227A) and a second prong (227B). Locking member (234) is sized to fit between first prong (227A) and second prong (227B) of two-prong member (227). Locking member (234) comprises a pair of projections (234A, 234B) that extend from opposite sides of locking member (234). Projections (234A, 234B) of locking member (234) rest upon a top surface of each prong (227A, 227B) such that two-prong member (227) holds locking member (234) between first prong (227A) and second prong (227B). A bottom surface of locking member (234) presents a plurality of teeth (239) configured to engage plurality of teeth (286) of second arm (280). A top surface of locking member (234) presents a circular bore (235) that extends partially through locking member (234). A spring (236) is positioned within bore (235) of locking member (234). Spring (236) of locking member (234) is bound on the upper side by an interior top surface of lateral slot (266) of first arm (260) as seen in FIG. 25. The configuration of spring (236) imparts a downward bias to locking member (234) and consequently the second end of lever (226) via two-prong member (227). As will be appreciated from the discussion below, this downward bias causes plurality of teeth (239) of locking member (234) to engage plurality of teeth (286) of second arm (280).

Pin (228) passes through lateral portion (264) of first arm (260) including lateral slot (266) as shown in FIG. 27. A portion of pin (228) is exposed within lateral slot (266). When skull clamp (200) is assembled, a bottom surface of lever (226) rests on the portion of pin (228) exposed within lateral slot (266). Pin (228) creates a pivoting axis about which lever (226) can rotate as will be discussed further below. A bore (231) is formed in a portion of lever (226) between the second end of lever (226) and pin (228). Screw (230) is positioned to extend through bore (231) and connect with a threaded bore in first arm (260). Spring (232) is disposed about screw (230) before it connects with first arm (260) such that spring (232) is bound on the upper side by the interior top surface of first arm (260) as seen in FIG. 26. The configuration of spring (232) imparts a downward bias to the second end of lever (226).

Figure 24B:
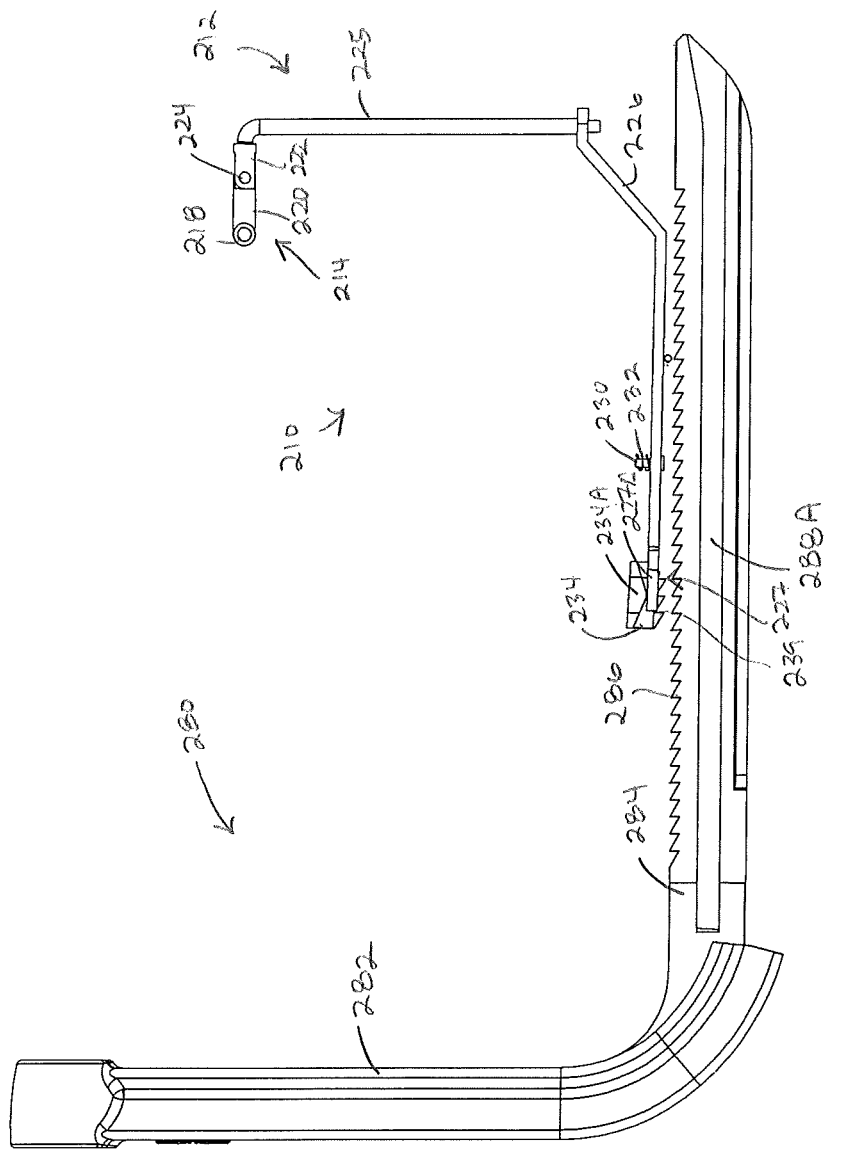
FIG. 24B depicts a side view of a second arm and the opening device of the skull clamp or FIG. 10, shown with the opening device disengaged from the second arm.

FIGS. 24-27 illustrate other views that further show features and operability of opening device (210). FIG. 24 illustrates a view with first arm (260) omitted to reveal how opening device (210) engages with second arm (280). In FIG. 24A, opening device (210) is engaged with plurality of teeth (286) such that arms (260, 280) cannot be opened or moved further away from one another. FIG. 24B illustrates a similar view, but this time with opening device (210) not engaged with plurality of teeth (286) such that arms (260, 280) can be opened or moved further away from one another. To achieve this opening, a user would first rotate trigger (214) of actuator (212) downward into the open position to remove it from the safety position within recessed space (263) of first arm (260). Then a user can push downward on trigger (214). This downward vertical translation causes rod (225) to translate vertically downward as well. Because of the connection between rod (225) and the first end of lever (226), downward vertical translation of rod (225) causes downward movement of the first end of lever (226). Downward movement of the first end of lever (226) causes clock-wise rotation of lever (226) about pin (228), such that the second end of lever (226) moves upward. The upward movement of the second end of lever (226) carries locking member (234) upward as well, and away from plurality of teeth (286) of second arm (280) to the point where plurality of teeth (239) of locking member (234) disengages plurality of teeth (286) on second arm (280). With such disengagement, arms (260, 280) can be opened and/or adjusted relative to one another. When opening or adjustment is complete, the user can remove the downward force applied to trigger (214) and opening device (210) will go through the reverse motion because of the downward bias from springs (236, 232) on the second end of lever (226). As seen in FIG. 27, there is space within first arm (260) above lever (226) when opening device (210) is engaged to secure arms (260, 280) such that lever (226) can pivot upward when opening device (210) is operated.

In one exemplary use of skull clamp (200), a single user can open or adjust the skull clamp without being aided by another person. For instance, a user grasps upright portions (262, 282) of each arm (260, 280) with their hands. In this position, the user can use a thumb to rotate trigger (214) of actuator (212) of opening device (210) downward so that opening device (210) is operable. At this point, the user can use the thumb to apply a downward force or pressure to trigger (214) of actuator (212) of opening device (210). As described above, this action causes plurality of teeth (239) of locking member (234) to disengage plurality of teeth (286) of second arm (280). At this point the user can apply outward force or pressure to arms (260, 280) to increase the distance between the arms to either fully open skull clamp (200) or to adjust skull clamp (200) to a larger position or size. The user may instead apply inward force or pressure to arms (260, 280) to decrease or close the distance between arms (260, 280). Once skull clamp (200) is at the desired position or size, the user releases the downward force on trigger (214) of actuator (212) and plurality of teeth (239) of locking member (234) engages plurality of teeth (286) of second arm (280) again to secure arms (260, 280) from further outward movement.

Figure 16:
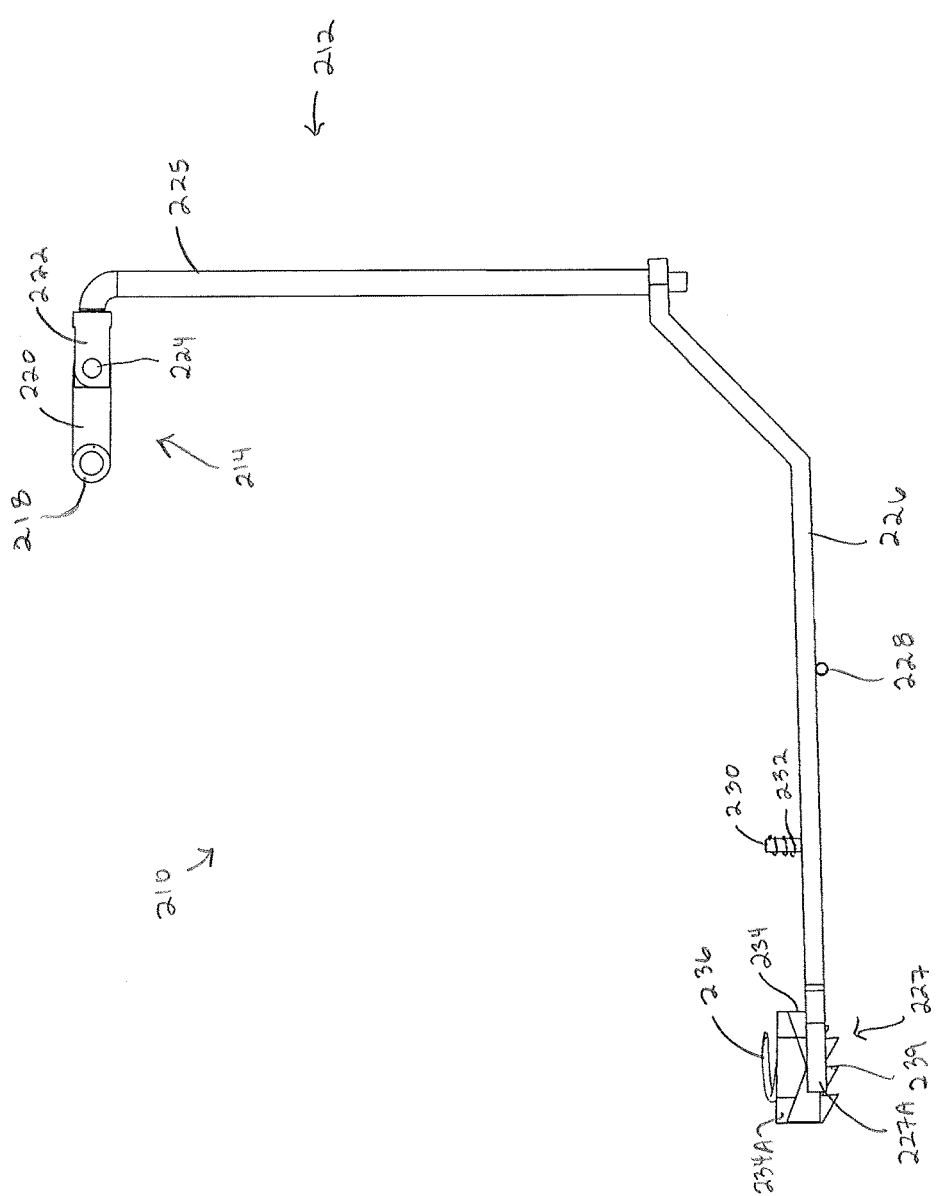
FIG. 16 depicts a side view of the opening device of FIG. 10.
Figure 17:
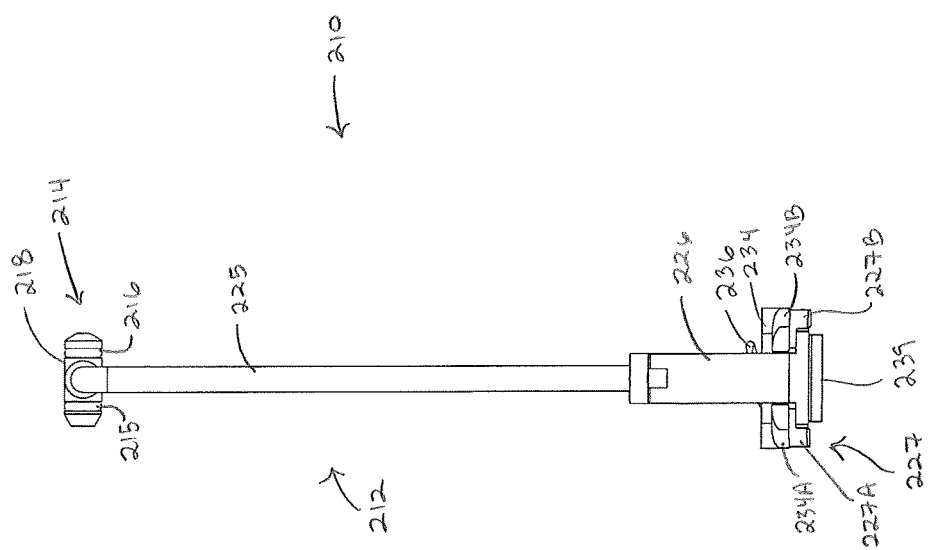
FIG. 17 depicts another side view of the opening device of FIG. 10.
Figure 18:
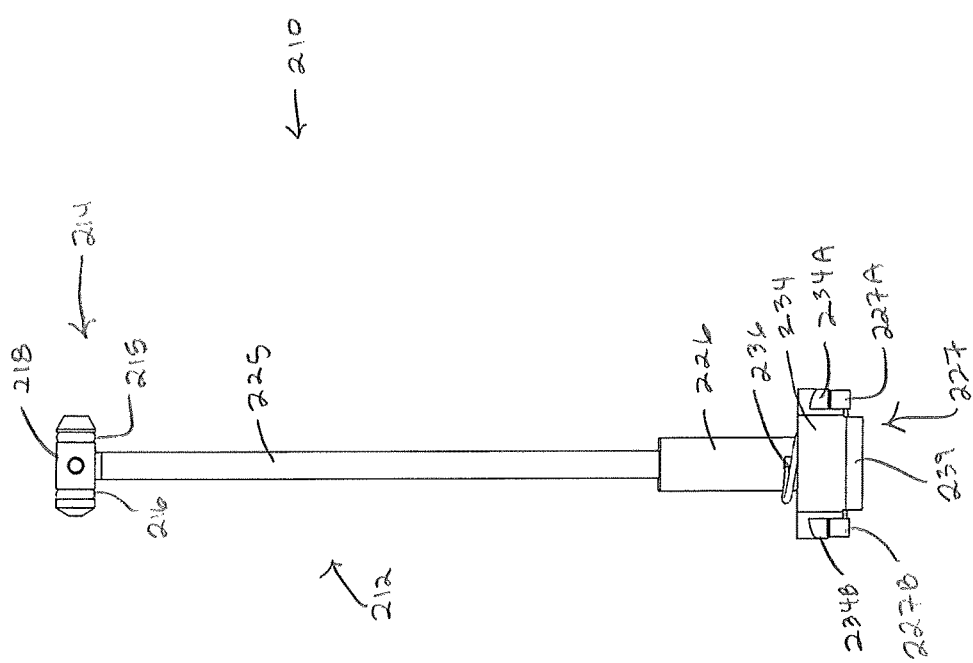
FIG. 18 depicts yet another side view of the opening device of FIG. 10.
Figure 19:
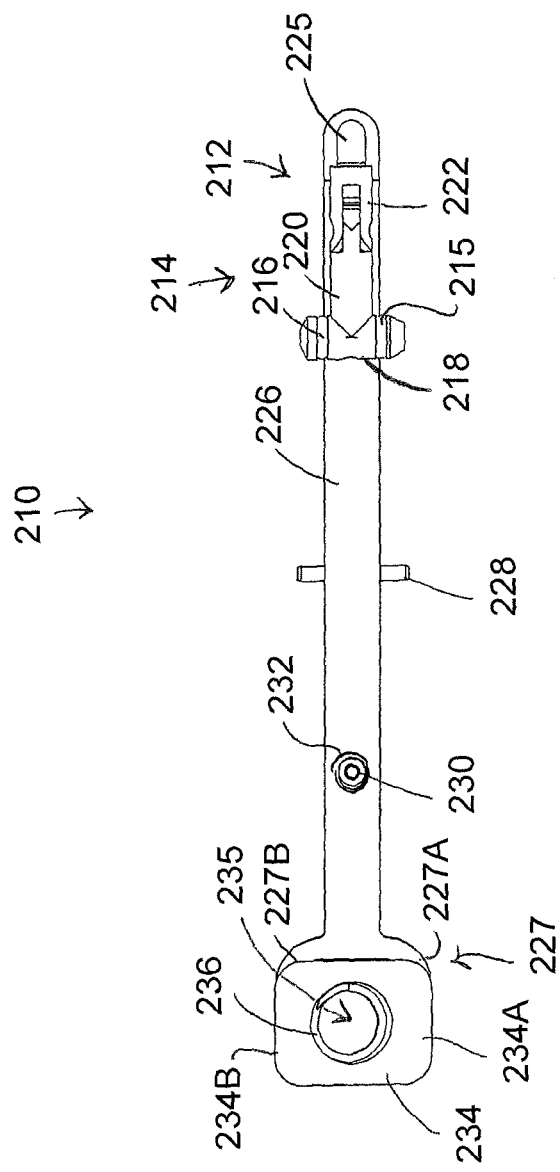
FIG. 19 depicts a top view of the opening device of FIG. 10.
Figure 20:
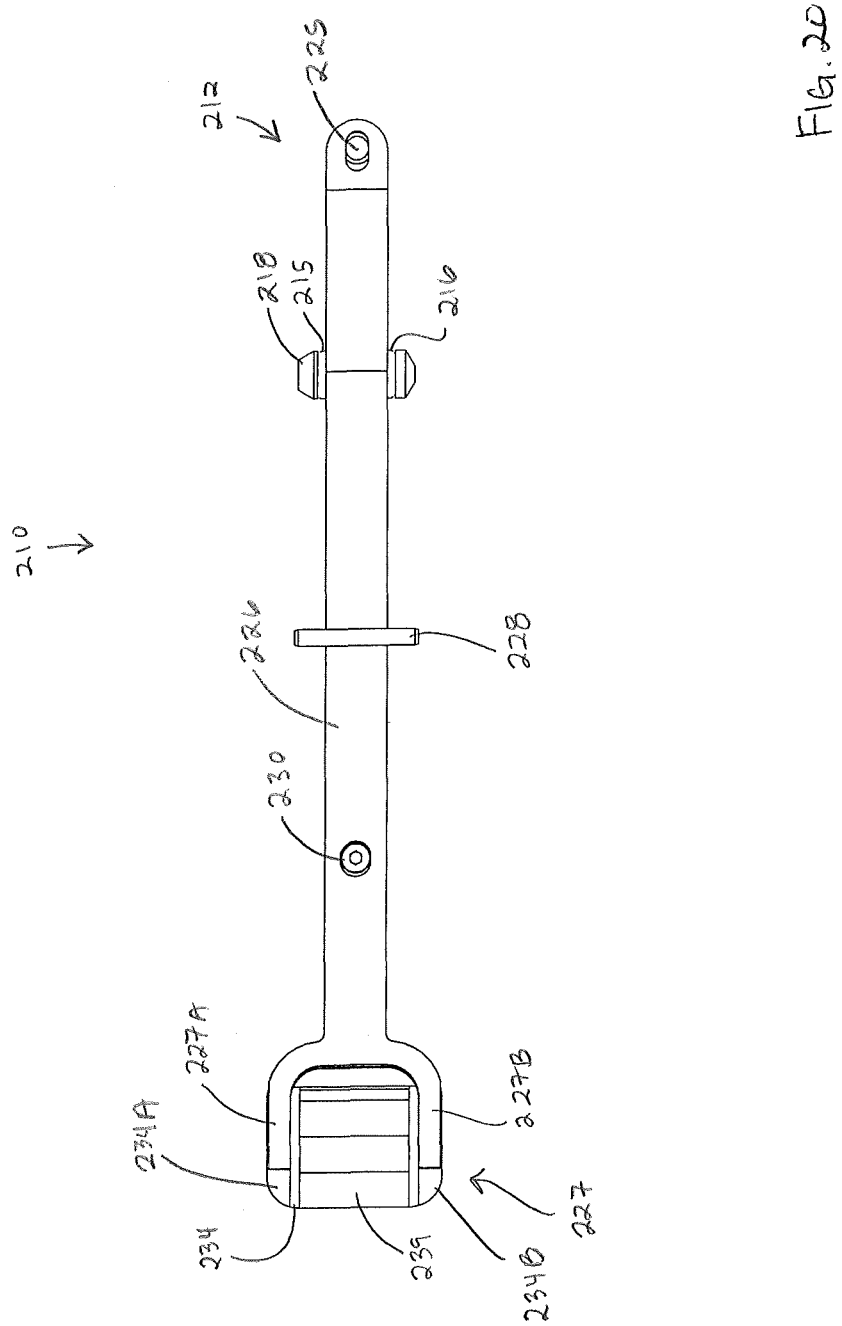
FIG. 20 depicts a bottom view of the opening device of FIG. 10.

When first positioning arms (260, 280) such that second arm (280) slides within first arm (260), or when closing arms (260, 280) generally (also referred to as shortening or reducing the distance between the arms), certain features maintain the position of certain components of opening device (210). As seen from the figures, the orientation of plurality of teeth (286) of second arm (280) and plurality of teeth (239) of locking member (234) will permit a user to move the arms closer together without the need to use trigger (214) of actuator (212) of opening device (210). In this action, the orientation and slope of plurality of teeth (286) of second arm (280) and plurality of teeth (239) of locking member (234) drive locking member (234) upward. This disengages plurality of teeth (239) of locking member (234) from plurality of teeth (286) of second arm (280) sufficiently such that skull clamp (200) can be made smaller (i.e. the space between upright portions (262, 282) of arms (260, 280) are closer as skull clamp (200) gets smaller). The configuration of the connection between lever (226) and locking member (234), and the configuration of first arm (260), allow locking member (234) to move during this closing action while lever (226) and most other components of opening device (210) remain generally stationary. More specifically, two-prong member (227) of lever (226) fits against locking member (234) along projections (234A, 234B) of locking member (234) as seen in FIGS. 15, 16, and 18. Plurality of teeth (239) of locking member (234) extend below two-prong member (227) of lever (226). Also, as shown in FIG. 25, there is a space between the interior top surface of first arm (260) and the top surface of locking member (234). Thus, moving arms (260, 280) closer together causes locking member (234) to move upward, compressing spring (236) shown in FIG. 25. At the same time, lever (226) remains substantially or completely stationary. Furthermore, spring (232) shown in FIG. 26 biases lever (226) in the downward position, helping to retain lever (226) in this downward position unless the bias of springs (236, 232) is sufficiently overcome.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

We claim:

1. A skull clamp comprising:
   (a) an opening device, wherein the opening device comprises an actuator, wherein at least a portion of the actuator is positioned along an upright portion of the skull clamp; and
   (b) a locking device, wherein at least a portion of the locking device is positioned along a lateral portion of the skull clamp, wherein movement of the actuator moves the locking device, wherein movement of the locking device selectively locks the skull clamp.

2. The skull clamp of claim 1, further comprising an attachment feature, wherein the attachment feature comprises a first starburst having a first bore and a second starburst having a second bore, wherein the first and second starbursts are positioned in opposing directions, wherein the first bore and the second bore are offset from one another.

3. The skull clamp of claim 2 wherein the first and the second starbursts are positioned along a lateral portion of a first arm of the skull clamp in a partial overlapping orientation yet with the first bore and the second bore offset from one another.

4. The skull clamp of claim 1, wherein the actuator comprises a pivoting trigger rotatable between a closed position and an open position.

5. The skull clamp of claim 4, wherein when the pivoting trigger is in the open position the pivoting trigger is in a substantially horizontal orientation.

6. The skull clamp of claim 4, wherein when the pivoting trigger is in the open position the pivoting trigger is accessible for actuation.

7. The skull clamp of claim 1, wherein the locking device comprises a lever, wherein the lever is rotatable between a locked position and an unlocked position.

8. The skull clamp of claim 7, wherein the actuator comprises a pivoting trigger rotatable between a closed position and an open position, wherein vertical translation of the pivoting trigger causes rotation of the lever between the locked position and the unlocked position.

9. The skull clamp of claim 1, wherein the locking device further comprises a first plurality of teeth.

10. The skull clamp of claim 9, wherein the lateral portion of the skull clamp comprises a second plurality of teeth configured to mate with the first plurality of teeth of the locking device.

11. The skull clamp of claim 10, wherein the first plurality of teeth of the locking device and the second plurality of teeth of the lateral portion are configured to prevent the skull clamp from moving in a first direction and to allow the skull clamp to move in a second direction.

12. The skull clamp of claim 1, wherein the actuator comprises a trigger portion positioned proximate to a pin holder assembly of a first arm of the skull clamp, and wherein the locking device is coupled with the actuator, wherein the locking device is positioned within the first arm of the skull clamp, wherein the locking device engages a second arm of the skull clamp to permit selective adjustment of the position of the first and second arms of the skull clamp relative to each other.

13. The skull clamp of claim 12, wherein the opening device is substantially disposed within the first arm of the skull clamp.

14. The skull clamp of claim 12, wherein the actuator is movable between an accessible position and an inaccessible position.

15. The skull clamp of claim 12, wherein engagement of the locking device with the second arm allows movement of the skull clamp toward a closed position and prevents movement of the skull clamp toward an opened position.

16. A skull clamp comprising an opening device, wherein the opening device comprises an actuator, wherein at least a portion of the actuator is positioned along an upright portion of the skull clamp, wherein the actuator comprises a pivoting trigger rotatable between a closed position and an open position, and wherein when the pivoting trigger is in the closed position the pivoting trigger is substantially disposed within the upright portion of the skull clamp.

17. A skull clamp comprising an opening device, wherein the opening device comprises an actuator, wherein at least a portion of the actuator is positioned along an upright portion of the skull clamp, wherein the actuator comprises a pivoting trigger rotatable between a closed position and an open position, and wherein the actuator further comprises an elongate member disposed within the upright portion of the skull clamp.

18. The skull clamp of claim 17, wherein vertical translation of the pivoting trigger causes vertical translation of the elongate member.

19. The skull clamp of claim 17, further comprising an attachment feature for connecting the skull clamp with other structures, wherein the attachment feature is formed as part of a lateral portion of a first arm of the skull clamp and comprises:
   (a) a first starburst having a first bore;
   (b) a second starburst having a second bore;
   (c) wherein the first and second starbursts are positioned in opposing directions; and
   (d) wherein the first bore and the second bore are offset from one another.

20. The skull clamp of claim 19 wherein the first and the second starbursts are positioned along the lateral portion of the first arm of the skull clamp in a partial overlapping orientation yet with the first bore and the second bore offset from one another.

* * * * *